US012729399B2

(12) United States Patent
Chen et al.

(10) Patent No.: US 12,729,399 B2
(45) Date of Patent: Sep. 8, 2026

(54) SYSTEMS AND METHODS FOR ASSESSING BIOLOGICAL SAMPLES

(71) Applicant: Life Technologies Corporation, Carlsbad, CA (US)

(72) Inventors: Mingsong Chen, Singapore (SG); Soo Yong Lau, Singapore (SG); Kuan Moon Boo, Singapore (SG); Mauro Aguanno, Singapore (SG); Huei Yeo, Singapore (SG); Tiong Han Toh, Singapore (SG); Wei Fuh Teo, Johor Bahru (MY)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 18/583,747

(22) Filed: Feb. 21, 2024

(65) Prior Publication Data

US 2024/0309441 A1 Sep. 19, 2024

Related U.S. Application Data

(62) Division of application No. 17/151,657, filed on Jan. 18, 2021, now Pat. No. 11,920,191, which is a
(Continued)

(51) Int. Cl.
*C12Q 1/686* (2018.01)
*B01L 7/00* (2006.01)
(Continued)

(52) U.S. Cl.
CPC ................ *C12Q 1/686* (2013.01); *B01L 7/52* (2013.01); *G01N 21/6428* (2013.01);
(Continued)

(58) Field of Classification Search
CPC ......... B01L 2200/10; B01L 2300/0654; B01L 2300/0829; B01L 2300/168;
(Continued)

(56) References Cited

U.S. PATENT DOCUMENTS 5,169,601 A 12/1992 Ohta et al.
5,672,881 A 9/1997 Striepeke et al.
(Continued)

FOREIGN PATENT DOCUMENTS

CN 101393313 A 3/2009
CN 101419156 A 4/2009
(Continued)

OTHER PUBLICATIONS

EP20171301.3, Extended European Search Report, Oct. 26, 2020, 35 pages.
(Continued)

*Primary Examiner* — Lydia Edwards

(57) ABSTRACT

An instrument for biological analysis includes a base, an excitation source, an optical sensor, an excitation optical system, and an emission optical system. The base is configured to receive a sample holder comprising a plurality of biological samples. The optical sensor is configured to receive emissions from the biological samples in response to the excitation source. The instrument may additionally include a sensor lens enclosed by a lens case and a focusing mechanism including a gear that engages the lens case, the focusing mechanism being accessible outside the enclosure for adjusting a focus. The instrument may further include a sensor aperture dispose along an emission optical path and a blocking structure disposed to cooperate with the sensor aperture such that none of the reflected radiation from an
(Continued)

illuminated surface near the sample holder is received by the optical sensor that does not also reflect off another surface of the instrument.

15 Claims, 14 Drawing Sheets

Related U.S. Application Data division of application No. 15/017,488, filed on Feb. 5, 2016, now abandoned.

(60) Provisional application No. 62/112,910, filed on Feb. 6, 2015.

(51) Int. Cl.
*B01L 99/00* (2010.01)
*G01N 21/64* (2006.01)
*G02B 21/24* (2006.01)

(52) U.S. Cl.
CPC ..... *G01N 21/6452* (2013.01); *G01N 21/6456* (2013.01); *G01N 21/6458* (2013.01); *G02B 21/244* (2013.01); *B01L 2200/10* (2013.01); *B01L 2300/0654* (2013.01); *B01L 2300/0829* (2013.01); *B01L 2300/168* (2013.01); *B01L 2300/18* (2013.01); *G01N 2021/6463* (2013.01)

(58) Field of Classification Search
CPC .................. B01L 2300/18; B01L 7/52; G01N 2021/6463; G01N 21/0332; G01N 21/6428; G01N 21/6452; G01N 21/6456; G01N 21/6458; G02B 21/244
See application file for complete search history.

(56) References Cited

U.S. PATENT DOCUMENTS

| | | | |
|---|---|---|---|
| 5,932,872 | A | 8/1999 | Price |
| 6,061,524 | A | 5/2000 | Uno |
| 6,180,948 | B1 | 1/2001 | Gutekunst et al. |
| 6,236,456 | B1 | 5/2001 | Giebeler et al. |
| 6,646,678 | B1 | 11/2003 | Kobayashi |
| 6,970,240 | B2 | 11/2005 | Oldham et al. |
| 7,148,043 | B2 | 12/2006 | Kordunsky et al. |
| 7,307,802 | B2 | 12/2007 | Unger |
| 7,324,202 | B2 | 1/2008 | Leonard et al. |
| 7,382,532 | B2 | 6/2008 | Okugawa |
| 7,383,078 | B2 | 6/2008 | Cable et al. |
| 7,387,891 | B2 | 6/2008 | Boege et al. |
| 7,417,803 | B2 | 8/2008 | Costigan et al. |
| 7,423,750 | B2 | 9/2008 | Hoshizaki et al. |
| 7,628,958 | B2 | 12/2009 | Tamaoki et al. |
| 7,635,588 | B2 | 12/2009 | King et al. |
| 7,812,944 | B1 | 10/2010 | Schmidt |
| 7,906,767 | B2 | 3/2011 | Furlan et al. |
| 8,108,031 | B2 | 1/2012 | Georgakoudi et al. |
| 8,211,660 | B2 | 7/2012 | Lin et al. |
| 8,431,389 | B2 | 4/2013 | Battrell et al. |
| 8,765,475 | B2 | 7/2014 | Zhou et al. |
| 8,791,427 | B2 | 7/2014 | Honda et al. |
| 8,809,040 | B2 | 8/2014 | King et al. |
| 8,987,685 | B2 | 3/2015 | Fawcett et al. |
| 9,157,860 | B2 | 10/2015 | Boege |
| 2003/0214581 | A1 | 11/2003 | Ikami |
| 2004/0014202 | A1 | 1/2004 | King et al. |
| 2004/0038390 | A1 | 2/2004 | Boege et al. |
| 2004/0063162 | A1 | 4/2004 | Dunlay et al. |
| 2004/0178370 | A1 | 9/2004 | Oldham et al. |
| 2004/0224317 | A1 | 11/2004 | Kordunsky et al. |
| 2005/0148846 | A1 | 7/2005 | Cable et al. |
| 2006/0006067 | A1 | 1/2006 | Unger |
| 2006/0006344 | A1 | 1/2006 | Boege |
| 2006/0072190 | A1 | 4/2006 | Okugawa |
| 2006/0103755 | A1 | 5/2006 | Costigan et al. |
| 2006/0119845 | A1 | 6/2006 | Leonard et al. |
| 2006/0121602 | A1 | 6/2006 | Hoshizaki et al. |
| 2007/0031290 | A1 | 2/2007 | Tamaoki et al. |
| 2007/0299327 | A1 | 12/2007 | Georgakoudi et al. |
| 2008/0258041 | A1 | 10/2008 | Mitani |
| 2009/0080057 | A1 | 3/2009 | Huang |
| 2009/0104710 | A1 | 4/2009 | Zhou et al. |
| 2009/0166570 | A1 | 7/2009 | Honda et al. |
| 2009/0201577 | A1 | 8/2009 | LaPlante et al. |
| 2010/0019157 | A1 | 1/2010 | Furlan et al. |
| 2010/0136709 | A1 | 6/2010 | Ruckstuhl et al. |
| 2010/0233092 | A1 | 9/2010 | Lin et al. |
| 2011/0057117 | A1 | 3/2011 | Fawcett et al. |
| 2011/0284765 | A1 | 11/2011 | Pieper et al. |
| 2012/0115214 | A1 | 5/2012 | Battrell et al. |
| 2013/0020506 | A1 | 1/2013 | Gruler |
| 2013/0034859 | A1 | 2/2013 | Boege et al. |
| 2014/0248693 | A1 | 9/2014 | Maher |
| 2016/0230210 | A1 | 8/2016 | Chen et al. |

FOREIGN PATENT DOCUMENTS

| | | | |
|---|---|---|---|
| CN | 201622245 | U | 11/2010 |
| CN | 102243107 | A | 11/2011 |
| CN | 104105957 | A | 10/2014 |
| CN | 104143156 | A | 11/2014 |
| EP | 0640828 | A1 | 3/1995 |
| EP | 2148188 | A1 | 1/2010 |
| EP | 2264439 | A2 | 12/2010 |
| EP | 2315002 | A2 | 4/2011 |
| EP | 2315002 | A3 | 12/2012 |
| EP | 2821779 | A1 | 1/2015 |
| JP | H02293651 | A | 12/1990 |
| JP | H05149789 | A | 6/1993 |
| JP | H07318427 | A | 12/1995 |
| JP | 2007504477 | A | 3/2007 |
| JP | 2008520975 | A | 6/2008 |
| JP | 2008261842 | A | 10/2008 |
| JP | 2009505070 | A | 2/2009 |
| JP | 2009254256 | A | 11/2009 |
| JP | 2010032513 | A | 2/2010 |
| JP | 2010142570 | A | 7/2010 |
| JP | 2011158419 | A | 8/2011 |
| JP | 2015006203 | A | 1/2015 |
| JP | 2015007754 | A | 1/2015 |
| KR | 20090046294 | A | 5/2009 |
| WO | WO-9848262 | A1 | 10/1998 |
| WO | WO-03098279 | A2 | 11/2003 |
| WO | WO-2006055521 | A2 | 5/2006 |
| WO | WO-2010088514 | A1 | 8/2010 |
| WO | WO-2010118541 | A1 | 10/2010 |
| WO | WO-2013049709 | A1 | 4/2013 |
| WO | WO-2013133725 | A1 | 9/2013 |
| WO | WO-2013138685 | A1 | 9/2013 |
| WO | WO-2013144359 | A2 | 10/2013 |

OTHER PUBLICATIONS

EP23155042.7, Extended European Search Report, Jul. 10, 2023, 10 pages.
Kwon K., et al., "Fluorescence Detection System with Miniaturized Integrating Sphere," Optical MEMS and Nanophotonics (OMN), 2011 International Conference on IEEE, Aug. 8, 2011, pp. 235-236, XP031968779.
Office Action for Indian Application No. 201717028360, dated Oct. 21, 2020, 6 pages.
Office Action for Japanese Application No. 2017-541370, dated Dec. 24, 2019, 13 pages.
Office Action issued in Korean Application No. 10-2017-7024924 dated Jan. 27, 2022, 12 pages.
Partial European Search Report for European Application No. 20171301.3, dated Aug. 18, 2020, 20 pages.
PCT/US2016/016886, International Preliminary Report on Patentability, Aug. 8, 2017, 18 pages.

(56) References Cited

OTHER PUBLICATIONS

PCT/US2016/016886, International Search Report and Written Opinion, Jul. 5, 2016, 28 pages.
Written Opinion for Singapore Application No. 11201706367W, dated May 28, 2018, 9 pages.
EP25163500.9, Extended European Search Report, May 30, 2025, 18 pages.
Singapore Appl. No. 10202103903U, Search Report and Written Opinion dated May 16, 2025, 7 pages.
Larson J., et al., "Design and Construction of a Multi-wavelength, Micromirror Total Internal Reflectance Fluorescence Microscope," Nature Protocols, Sep. 4, 2014, vol. 9, No. 10, pp. 2317-2328.
Mathies R.A., et al., "Laser-Excited Confocal-fluorescence Gel Scanner," Review of Scientific Instruments, American Institute of Physics, Apr. 1, 1994, vol. 65, No. 4, Part 01, XP000447665, pp. 807-812.

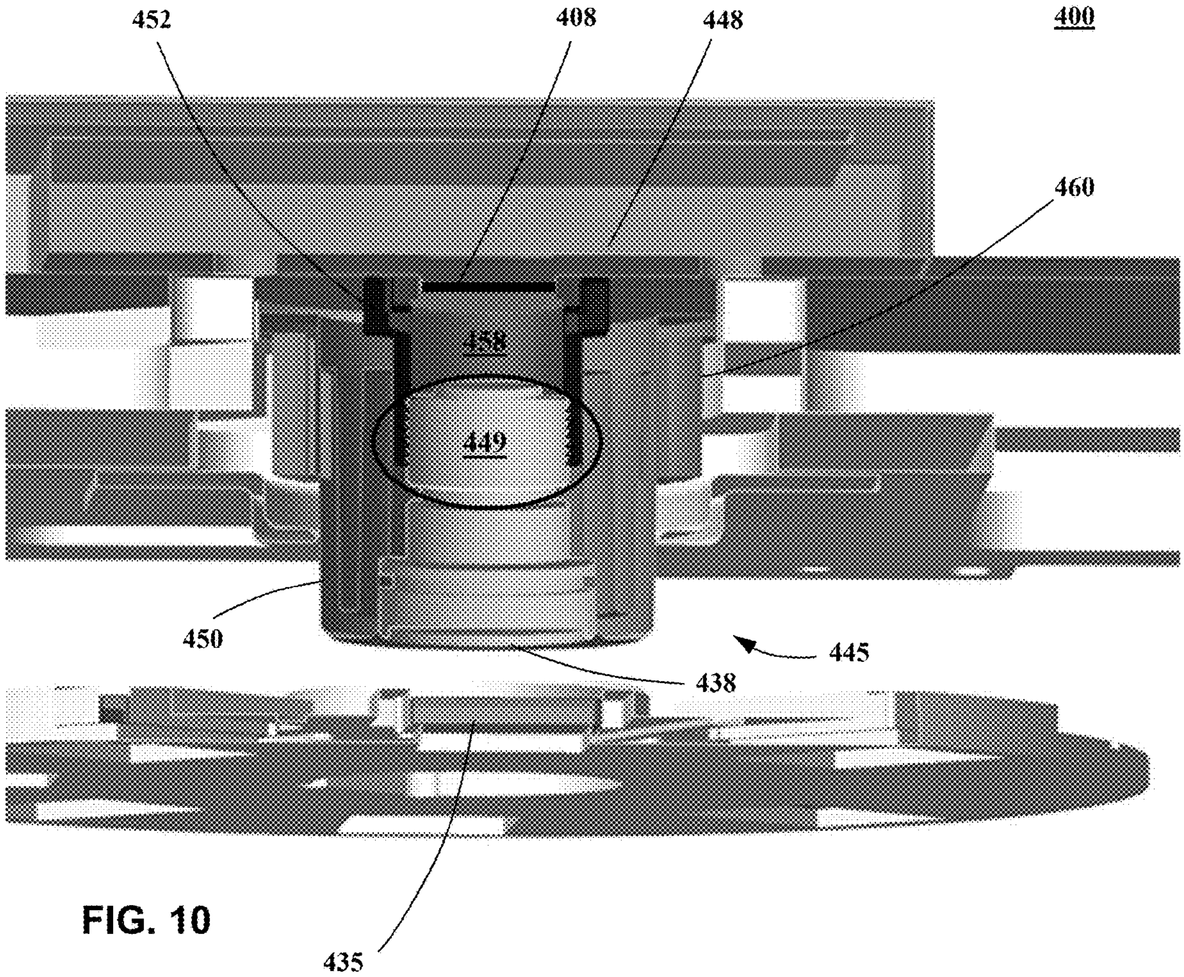
FIG. 10
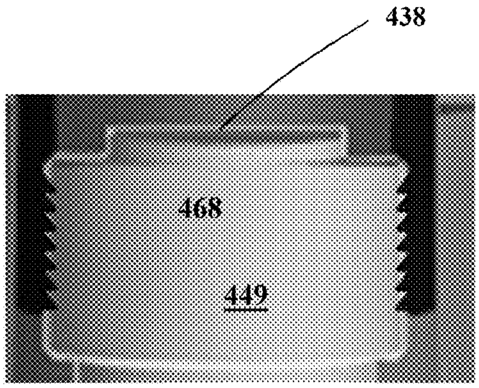

FIG. 15
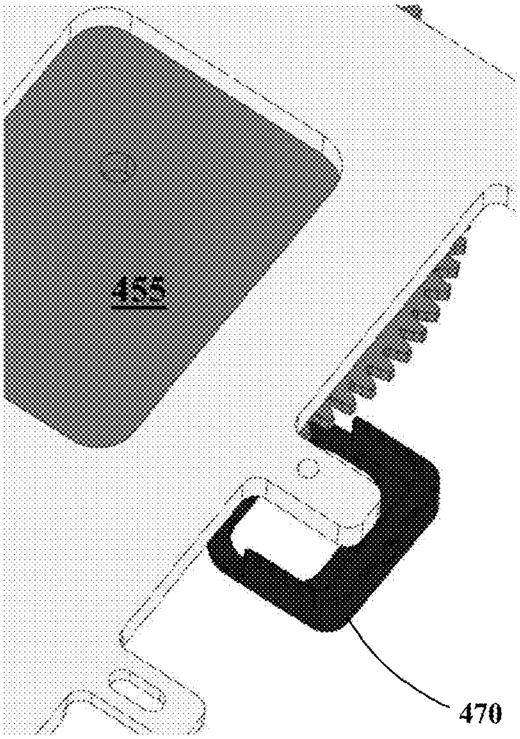
FIG. 16
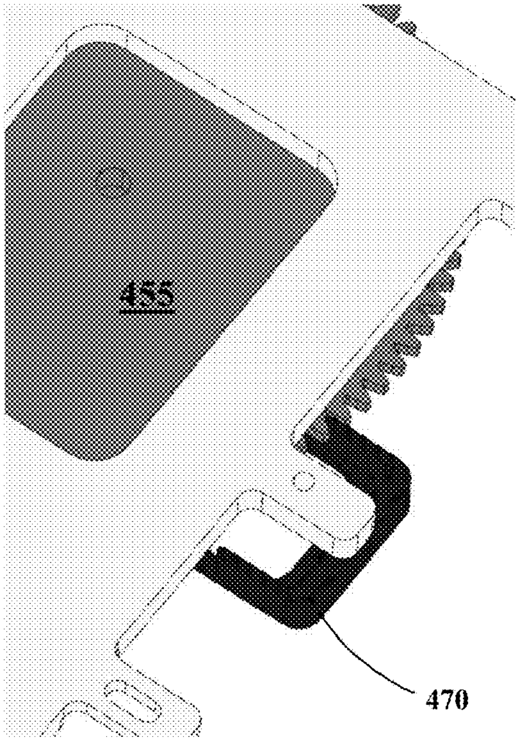
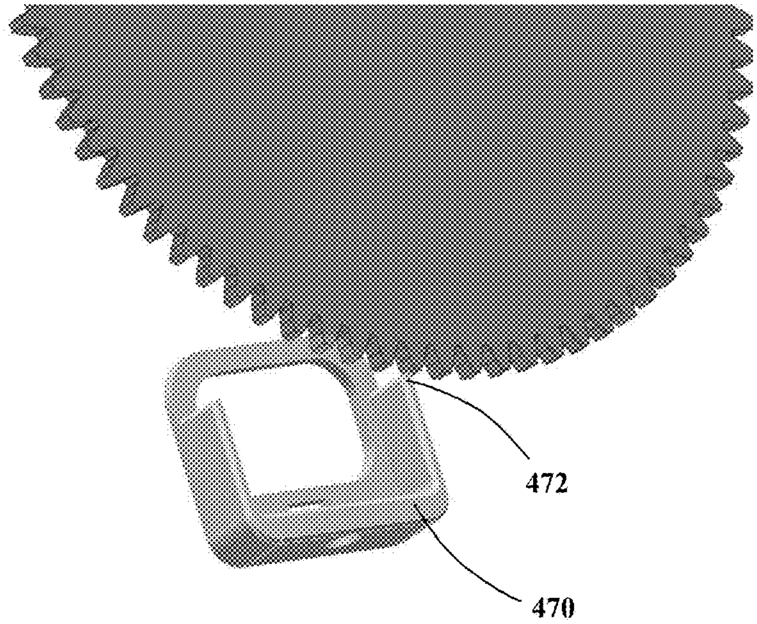
FIG. 17

SYSTEMS AND METHODS FOR ASSESSING BIOLOGICAL SAMPLES

CROSS-REFERENCE TO RELATED APPLICATIONS

This application is a divisional of U.S. application Ser. No. 17/151,657 filed Jan. 18, 2021, which is a divisional of U.S. application Ser. No. 15/017,488 filed Feb. 5, 2016 (now Abandoned), which claims the benefit of priority of U.S. Provisional Application No. 62/112,910 filed on Feb. 6, 2015, all of which are incorporated herein in their entirety by reference.

BACKGROUND OF THE INVENTION

Field of the Invention

The present invention relates generally to systems, devices, and methods for observing, testing, and/or analyzing one or more biological samples, and more specifically to systems, devices, and methods comprising an optical system for observing, testing, and/or analyzing one or more biological samples.

DESCRIPTION OF THE RELATED ART

N/A

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures:

FIG. 10 is a section view of a portion of the optical system shown in FIG. 7.

FIGS. 15-17 are magnified views of portions of the imaging unit shown in FIG. 11.

DETAILED DESCRIPTION OF THE DRAWINGS

Figure 1:
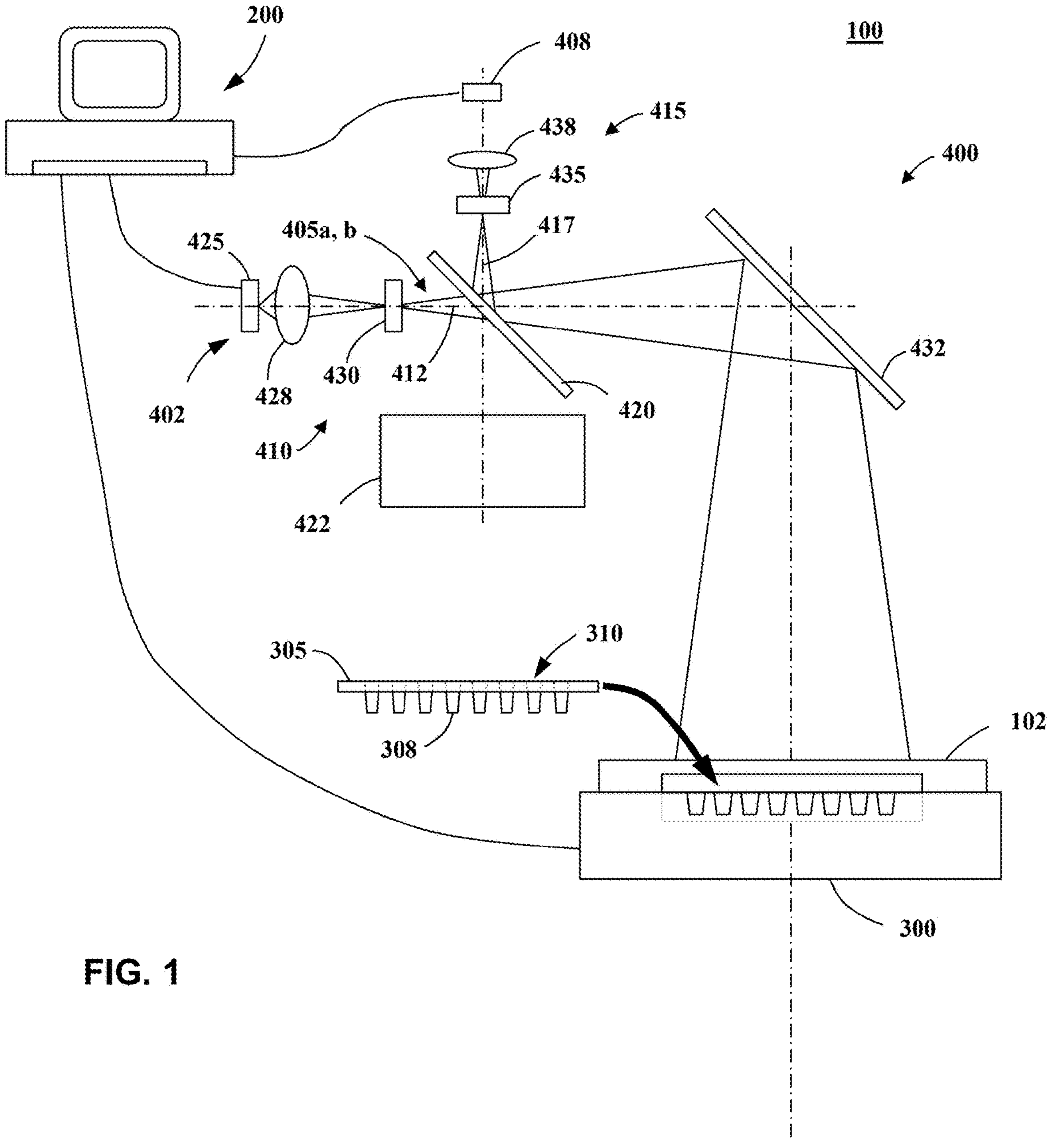
FIG. 1 is a schematic representation of a system according to an embodiment of the present invention.

As used herein the terms "radiation" or "electromagnetic radiation" means radiant energy released by certain electromagnetic processes that may include one or more of visible light (e.g., radiant energy characterized by one or more wavelengths between 400 nanometers and 700 nanometers or between 380 nanometers and 800 nanometers) or invisible electromagnetic radiations (e.g., infrared, near infrared, ultraviolet (UV), X-ray, or gamma ray radiation).

As used herein an excitation source means a source of electromagnetic radiation that may be directed toward at least one sample containing one or more chemical compounds such that the electromagnetic radiation interacts with the at least one sample to produce emission electromagnetic radiation indicative of a condition of the at least one sample. The excitation source may comprise light source. As used herein, the term "light source" refers to a source of electromagnetic radiation comprising an electromagnetic spectrum having a peak or maximum output (e.g., power, energy, or intensity) that is within the visible wavelength band of the electromagnetic spectrum (e.g., electromagnetic radiation within a wavelength in the range of 400 nanometers to 700 nanometers or in the range of 380 nanometers and 800 nanometers). Additionally or alternatively, the excitation source may comprise electromagnetic radiation within at least a portion of the infrared (near infrared, mid infrared, and/or far infrared) or ultraviolet (near ultraviolet and/or extreme ultraviolet) portions of the electromagnetic spectrum. Additionally or alternatively, the excitation source may comprise electromagnetic radiation in other wavelength bands of the electromagnetic spectrum, for example, in the X-ray and/or radio wave portions of the electromagnetic spectrum. The excitation source may comprise a single source of light, for example, an incandescent lamp, a gas discharge lamp (e.g., Halogen lamp, Xenon lamp, Argon lamp, Krypton lamp, etc.), a light emitting diode (LED), an organic LED (OLED), a laser, or the like. The excitation source may comprise a plurality of individual light sources (e.g., a plurality of LEDs or lasers). The excitation source may also include one or more excitation filters, such as a high-pass filter, a low-pass filter, or a band-pass filter. For example, the excitation filter may include a colored filter and/or a dichroic filter. The excitation source comprise a single beam or a plurality of beams that are spatially and/or temporally separated.

As used herein, an "emission" means an electromagnetic radiation produced as the result an interaction of radiation from an excitation source with one or more samples containing, or thought to contain, one or more chemical and/or biological molecules or compounds of interest. The emission may be due to a reflection, refraction, polarization, absorption, and/or other optical effect by the sample on radiation from the excitation source. For example, the emission may comprise a luminescence or fluorescence induced by absorption of the excitation electromagnetic radiation by one or more samples. As used herein "emission light" refers to an emission comprising an electromagnetic spectrum having a peak or maximum output (e.g., power, energy, or intensity) that is within the visible band of the electromagnetic spectrum (e.g., electromagnetic radiation within a wavelength in the range of 420 nanometers to 700 nanometers).

As used herein, a lens means an optical element configured to direct or focus incident electromagnetic radiation so as to converge or diverge such radiation, for example, to provide a real or virtual image, either at a finite distance or at an optical infinity. The lens may comprise a single optical element having an optical power provided by refraction, reflection, and/or diffraction of the incident electromagnetic radiation. Alternatively, the lens may comprise a compound system including a plurality of optical element, for example, including, but not limited to, an achromatic lens, doublet lens, triplet lens, or camera lens. The lens may be at least partially housed in or at least partially enclosed by a lens case or a lens mount.

As used herein, the term "optical power" means the ability of a lens or optic to converge or diverge light to provide a focus (real or virtual) when disposed within air. As used herein the term "focal length" means the reciprocal of the optical power. As used herein, the term "diffractive power" or "diffractive optical power" means the power of a lens or optic, or portion thereof, attributable to diffraction of incident light into one or more diffraction orders. Except where noted otherwise, the optical power of a lens, optic, or optical element is from a reference plane associated with the lens or optic (e.g., a principal plane of an optic).

As used herein, the term "biological sample" means a sample or solution containing any type of biological chemical or component and/or any target molecule of interest to a user, manufacturer, or distributor of the various embodiments of the present invention described or implied herein, as well as any sample or solution containing related chemicals or compounds used for the purpose of conducting a biological assay, experiment, or test. These biological chemicals, components, or target molecules may include, but are not limited to, DNA sequences (including cell-free DNA), RNA sequences, genes, oligonucleotides, molecules, proteins, biomarkers, cells (e.g., circulating tumor cells), or any other suitable target biomolecule. A biological sample may comprise one or more of at least one target nucleic acid sequence, at least one primer, at least one buffer, at least one nucleotide, at least one enzyme, at least one detergent, at least one blocking agent, or at least one dye, marker, and/or probe suitable for detecting a target or reference nucleic acid sequence. In various embodiments, such biological components may be used in conjunction with one or more PCR methods and systems in applications such as fetal diagnostics, multiplex dPCR, viral detection, and quantification standards, genotyping, sequencing assays, experiments, or protocols, sequencing validation, mutation detection, detection of genetically modified organisms, rare allele detection, and/or copy number variation.

According to embodiments of the present invention, one or more samples or solutions containing at least one biological targets of interest may be contained in, distributed between, or divided between a plurality of a small sample volumes or reaction regions (e.g., volumes or regions of less than or equal to 10 nanoliters, less than or equal to 1 nanoliter, or less than or equal to 100 picoliters). The reaction regions disclosed herein are generally illustrated as being contained in wells located in a substrate material; however, other forms of reaction regions according to embodiments of the present invention may include reaction regions located within through-holes or indentations formed in a substrate, spots of solution distributed on the surface a substrate, samples or solutions located within test sites or volumes of a capillary or microfluidic system, or within or on a plurality of microbeads or microspheres.

While devices, instruments, systems, and methods according to embodiments of the present invention are generally directed to dPCR and qPCR, embodiments of the present invention may be applicable to any PCR processes, experiment, assays, or protocols where a large number of reaction regions are processed, observed, and/or measured. In a dPCR assay or experiment according to embodiments of the present invention, a dilute solution containing at least one target polynucleotide or nucleotide sequence is subdivided into a plurality of reaction regions, such that at least some of these reaction regions contain either one molecule of the target nucleotide sequence or none of the target nucleotide sequence. When the reaction regions are subsequently thermally cycled in a PCR protocol, procedure, assay, process, or experiment, the reaction regions containing the one or more molecules of the target nucleotide sequence are greatly amplified and produce a positive, detectable detection signal, while those containing none of the target(s) nucleotide sequence are not amplified and do not produce a detection signal, or a produce a signal that is below a predetermined threshold or noise level. Using Poisson statistics, the number of target nucleotide sequences in an original solution distributed between the reaction regions may be correlated to the number of reaction regions producing a positive detection signal. In some embodiments, the detected signal may be used to determine a number, or number range, of target molecules contained in the original solution. For example, a detection system may be configured to distinguish between reaction regions containing one target molecule and reaction regions containing two or at least two target molecules. Additionally or alternatively, the detection system may be configured to distinguish between reaction regions containing a number of target molecules that is at or below a predetermined amount and reaction regions containing more than the predetermined amount. In certain embodiments, both qPCR and dPCR processes, assays, or protocols are conducted using a single the same devices, instruments, or systems, and methods.

Referring to FIG. 1, a system, apparatus, or instrument 100 for biological analysis comprises one or more of an electronic processor, computer, or controller 200, a base, mount, or sample block assembly 300 configured to receive and/or processes a biological or biochemical sample, and/or an optical system, apparatus, or instrument 400. Without limiting the scope of the present invention, system 100 may comprise a sequencing instrument, a polymerase chain reaction (PCR) instrument (e.g., a real-time PCR (qPCR) instrument and/or digital PCR (dPCR) instrument), capillary electrophoresis instrument, an instrument for providing genotyping information, or the like.

Electronic processor 200 is configured to control, monitor, and/or receive data from optical system 400 and/or base 300. Electronic processor 200 may be physically integrated into optical system 400 and/or base 300. Additionally or alternatively, electronic processor 200 may be separate from optical system 400 and base 300, for example, an external desktop computer, laptop computer, notepad computer, tablet computer, or the like. Communication between electronic processor 200 and optical system 400 and/or base 300 may be accomplished directly via a physical connection, such as a USB cable or the like, and/or indirectly via a wireless or network connection (e.g., via Wi-Fi connection, a local area network, internet connection, cloud connection, or the like). Electronic processor 200 may include electronic memory storage containing instructions, routines, algorithms, test and/or configuration parameter, test and/or experimental data, or the like. Electronic processor 200 may be configured, for example, to operate various components of optical system 400 or to obtain and/or process data provided by base 300. For example, electronic processor 200 may be used to obtain and/or process optical data provided by one or more photodetectors of optical system 400.

In certain embodiments, electronic processor 200 may integrated into optical system 400 and/or base 300. Electronic processor 200 may communicate with external computer and/or transmit data to an external computer for further processing, for example, using a hardwire connection, a local area network, an internet connection, cloud computing system, or the like. The external computer may be physical computer, such as a desktop computer, laptop computer, notepad computer, tablet computer, or the like, that is located in or near system 100. Additionally or alternatively, either or both the external computer and electronic processor 200 may comprise a virtual device or system, such as a cloud computing or storage system. Data may be transferred between the two via a wireless connection, a cloud storage or computing system, or the like. Additionally or alternatively, data from electronic processor 200 (e.g., from optical system 400 and/or base 300) may be transferred to an external memory storage device, for example, an external hard drive, a USB memory module, a cloud storage system, or the like.

In certain embodiments, base 300 is configured to receive a sample holder or sample carrier 305. Sample holder 305 may comprise a plurality or array of spatially separated reaction regions, sites, or locations 308 for containing a corresponding plurality or array of biological or biochemical samples 310. Reaction regions 308 may comprise any plurality of volumes or locations isolating, or configured to isolate, the plurality of biological or biochemical samples 310. For example, reaction regions 308 may comprise a plurality of through-hole or well in a substrate or assembly (e.g., sample wells in a standard microtiter plate), a plurality of sample beads, microbeads, or microspheres in a channel, capillary, or chamber, a plurality of distinct locations in a flow cell, a plurality of sample spots on a substrate surface, or a plurality of wells or openings configured to receive a sample holder (e.g., the cavities in a sample block assembly configured to receive a microtiter plate).

Base 300 may comprise a sample block assembly configured to control the temperature of sample holder 305 and/or biological samples 310. Sample block assembly 300 may comprise one or more of a sample block, a Peltier device or other apparatus for controlling or cycling temperature, and/or a heat sink (e.g., for aiding in stabilizing a temperature). Base 300 may comprise a thermal controller or thermal cycler, for example, to provide or perform a PCR assay.

Reaction apparatus 300 may include sample holder 305. At least some of the reaction regions 308 may include the one or more biological samples 310. Biological or biochemical samples 310 may include one or more of at least one target nucleic acid sequence, at least one primer, at least one buffer, at least one nucleotide, at least one enzyme, at least one detergent, at least one blocking agent, or at least one dye, marker, and/or probe suitable for detecting a target or reference nucleic acid sequence. Sample holder 305 may be configured to perform at least one of a PCR assay, a sequencing assay, or a capillary electrophoresis assay, a blot assay. In certain embodiments, sample holder 305 may comprise one or more of a microtiter plate, substrate comprising a plurality of wells or through-holes, a substrate comprising a one or more channels or capillaries, or a chamber comprising plurality of beads or spheres containing the one or more biological samples. Reaction regions 308 may comprise one or more of a plurality of wells, a plurality of through-holes in substrate, a plurality of distinct locations on a substrate or within a channel or capillary, a plurality of microbeads or microspheres within a reaction volume, or the like. Sample holder 305 may comprise a microtiter plate, for example, wherein reaction regions 308 may comprise at least 96 well, at least 384, or at least 1536 wells.

In certain embodiments, sample holder 305 may comprise a substrate including a first surface, an opposing second surface, and a plurality of through-holes disposed between the surfaces, the plurality of through-holes configured to contain the one or more biological samples, for example as discussed in Patent Application Publication Numbers US 2014-0242596 and WO 2013/138706, which applications are herein incorporated by reference as if fully set forth herein. In such embodiments, the substrate may comprise at least 3096 through-holes or at least 20,000 through-holes. In certain embodiments, sample holder 305 may comprise an array of capillaries configured to pass one or more target molecules or sequence of molecules.

In certain embodiments, system 100 may optionally include a heated or temperature controlled cover 102 that may be disposed above sample holder 305 and/or base 300. Heated cover 102 may be used, for example, to prevent condensation above the samples contained in sample holder 305, which can help to maintain optical access to biological samples 310. In certain embodiments, optical system 400 comprises an excitation source, illumination source, radiation source, or light source 402 that produces at least a first excitation beam **405*a* characterized by a first wavelength and a second excitation beam 405*b* characterized by a second wavelength that is different from the first wavelength. Optical system 400 also comprises an optical sensor or optical detector 408 configured to receive emissions or radiation from one or more biological samples in response to excitation source 410 and/or to one or more of excitation beams 405*a*, 405*b*. Optical system 400 additionally comprises an excitation optical system 410 disposed along an excitation optical path 412 between excitation source 402 and one or more biological samples to be illuminated. Optical system 400 further comprises an emission optical system 415 disposed along an emission optical path 417 between the illuminated sample(s) and optical sensor 408. In certain embodiments, optical system 400 may comprise a beamsplitter 420. Optical system 400 may optionally include a beam dump or radiation baffle 422 configured reduce or prevent reflection of radiation into emission optical path 417 from excitation source 402 that impinges on beamsplitter 420**.

In the illustrated embodiment shown in FIG. 1, as well as other embodiments of the invention disclosed herein, excitation source 402 comprises a radiation source 425. Radiation source 425 may comprise one or more of at least one an incandescent lamp, at least one gas discharge lamp, at least one light emitting diode (LED), at least one organic light emitting diode, and/or at least one laser. For example, radiation source 425 may comprise at least one Halogen lamp, Xenon lamp, Argon lamp, Krypton lamp, diode laser, Argon laser, Xenon laser, excimer laser, solid-state laser, Helium-Neon laser, dye laser, or combinations thereof. Radiation source 425 may comprise a light source characterized by a maximum or central wavelength in the visible band of the electromagnetic spectrum. Additionally or alternatively, radiation source 425 may comprise an ultraviolet, infrared, or near-infrared source with a corresponding maximum or central wavelength within on one of those wavelength bands of the electromagnetic spectrum. Radiation source 425 may be a broadband source, for example, having a spectral bandwidth of at least 100 nanometers, at least 200 nanometers, or at least 300 nanometers, where the bandwidth is defined as a range over which the intensity, energy, or power output is greater than a predetermined amount (e.g., where the predetermined amount is at or about 1%, 5%, or 10% of a maximum or central wavelength of the radiation source). Excitation source 402 may additionally comprise a source lens 428 configured to condition emissions from radiation source 425, for example, to increase the amount of excitation radiation received at sample holder 305 and/or into biological samples 310. Source lens 428 may comprise a simple lens or may be a compound lens including two or more elements.

In certain embodiments, excitation source 402 further comprises two or more excitation filters 430 moveable into and out of excitation optical path 412, for instance, used in combination with a broadband excitation source 402. In such embodiments, different excitation filters 430 may be used to select different wavelength ranges or excitation channels suitable for inducing fluorescence from a respective dye or marker within biological samples 310. One or more of excitation filters 430 may have a wavelength bandwidth that is at least ±10 nanometers or at least ±15 nanometers. Excitation filters 430 may comprise a plurality of filters that together provide a plurality of band passes suitable for fluorescing one or more of a SYBR® dye or probe, a FAM™ dye or probe, a VIC® dye or probe, a ROX™ dye or probe, or a TAMRA™ dye or probe. Excitation filters 430 may be arrange in a rotatable filter wheel (not shown) or other suitable device or apparatus providing different excitation channels using excitation source 402. In certain embodiments, excitation filters 430 comprise at least 5 filter or at least 6 filter.

In certain embodiments, excitation source 402 may comprise a plurality of individual excitation sources that may be combined using one more beamsplitters or beam combiners, such that radiation from each individual excitation source is transmitted along a common optical path, for example, along excitation optical path 412 shown in FIG. 1. Alternatively, at least some of the individual excitation sources may be arranged to provided excitation beams that propagate along different, non-overlapping optical paths, for example, to illuminate different reaction regions of the plurality of reaction regions 308. Each of the individual excitation sources may be addressed, activated, or selected to illuminate reaction regions 308, for example, either individually or in groups or all simultaneously. In certain embodiments, the individual excitation sources may be arranged in a one-dimensional or two-dimensional array, where one or more of the individual excitation sources is characterized by a maximum or central wavelength that is different than that of at least one of the other individual excitation sources in the array.

In certain embodiments, first excitation beam 405*a* comprises a first wavelength range over which an intensity, power, or energy of first excitation beam 405*a* is above a first predetermined value and second excitation beam 405*b* comprises a second wavelength range over which an intensity, power, or energy of second excitation beam 405*b* is above a second predetermined value. The characteristic wavelength of the excitation beams 405*a*, 405*b* may be a central wavelength of the corresponding wavelength range or a wavelength of maximum electromagnetic intensity, power, or energy over the corresponding wavelength range. The central wavelengths of at least one of the excitation beams 405 may be an average wavelength over the corresponding wavelength range. For each excitation beam 405 (e.g., excitation beams 405*a*, 405*b*), the predetermined value may be less than 20% of the corresponding maximum intensity, power, or energy; less than 10% of the corresponding maximum intensity, power, or energy; less than 5% of the corresponding maximum intensity, power, or energy; or less than 1% of the corresponding maximum intensity, power, or energy. The predetermined values may be the same for all excitation beams 405 (e.g., for both excitation beams 405*a*, 405*b*) or the predetermined values may be different from one another. In certain embodiments, the wavelength ranges of the first and second excitation beams 405*a*, 405*b* do not overlap, while in other embodiments at least one of the wavelength ranges at least partially overlaps that of the other. In certain embodiments, the first and second central wavelengths are separated by at least 20 nanometer. In certain embodiments, at least one of the first and second wavelength ranges has a value of at least 20 nanometer or at least 30 nanometers.

Excitation optical system 410 is configured to direct excitation beams 405*a*, 405*b* to the one or more biological samples. Where applicable, references herein to excitation beams 405*a*, 405*b* may be applied to embodiment comprising more than two excitation beams 405. For example, excitation source 402 may be configured to direct at least five or six excitation beams 405. Excitation beams 405*a*, 405*b* may be produced or provided simultaneously, may be temporally separated, and/or may be spatially separated (e.g., wherein excitation beams 405*a* is directed to one reaction region 308 and excitation beams 405*b* is directed to a different reaction region 308). The excitation beams 405 may be produced sequentially, for example, by sequentially turning on and off different-colored individual radiation source 425 that are characterized by different wavelengths or by sequentially placing different color filters in front of a single radiation source 425. Alternatively, excitation beams 405*a*, 405*b* may be produced simultaneously, for example, by using a multi-wavelength band filter, beamsplitter, or mirror, or by coupling together different individual radiation source 425, such as two different-colored light emitting diodes (LEDs). In some embodiments, excitation source 402 produces more than two excitation beams 405, wherein excitation optical system 410 directs each of the excitation beams to one or more biological samples 310.

Figure 2:
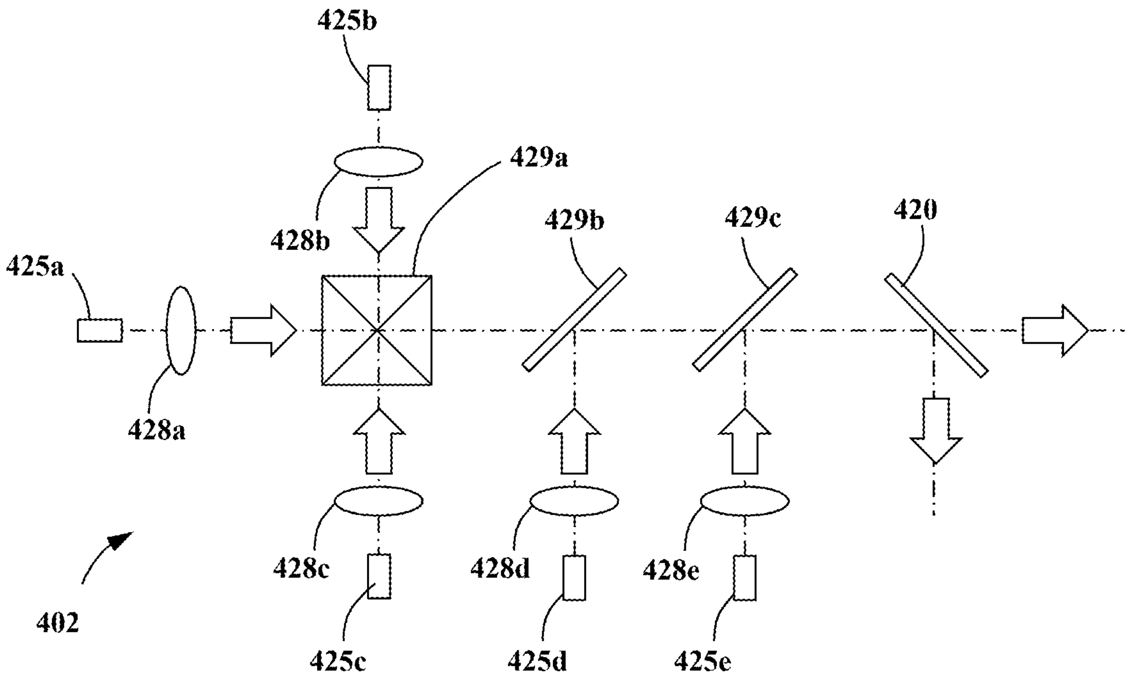
FIG. 2 is a schematic representation of an excitation source according to an embodiment of the present invention.

Referring to FIG. 2, excitation source 402 may comprise at least 5 individual radiant sources 425*a*, 425*b*, 425*c*, 425*d*, 425*e* that are combined to transmit along a common excitation optical path 412. Excitation source 402 may also comprise corresponding sources lenses 428*a*, 428*b*, 428*c*, 428*d*, 428*c*. Radiation from radiant sources 425*a*, 425*b*, 425*c*, 425*d*, 425*e* may be combined using a plurality of combiner optical elements 429*a*, 429*b*, 429*c*. Combiner optical elements 429*a*, 429*b*, 429*c* may comprise one or more of a neutral density filter, a 50/50 beamsplitter, a dichroic filter or mirror, a cube beamsplitter, or the like. Combiner optical elements 429*a*, 429*b*, 429*c* are one example of how to combine various individual sources 425 and it will be appreciated that other combinations and geometrical arrangements of individual radiant sources 425 and combiner optical elements 429 are within the scope of embodiments of the present invention. One or more of individual radiant sources 425*a*, 425*b*, 425*c*, 425*d*, 425*c* may be characterized by a central wavelength and/or wavelength range that is differ from that of the other individual radiant sources 425*a*, 425*b*, 425*c*, 425*d*, 425*c*.

Figure 3:
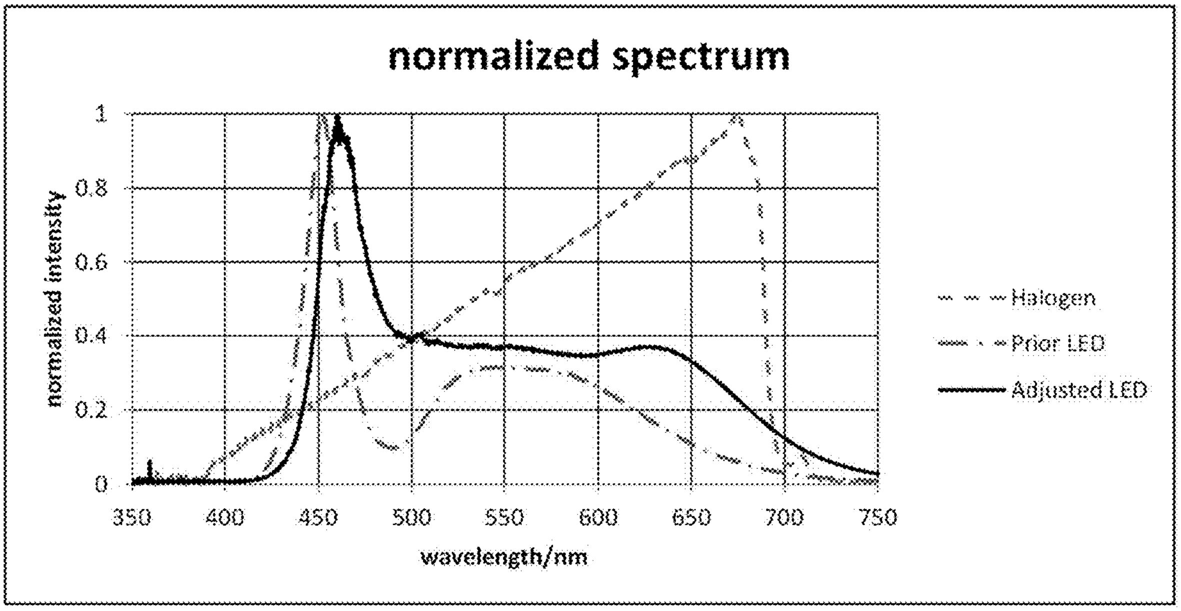
FIG. 3 is a normalized spectrum plot of various light sources, including a light source according to an embodiment of the present invention.
Figure 4:
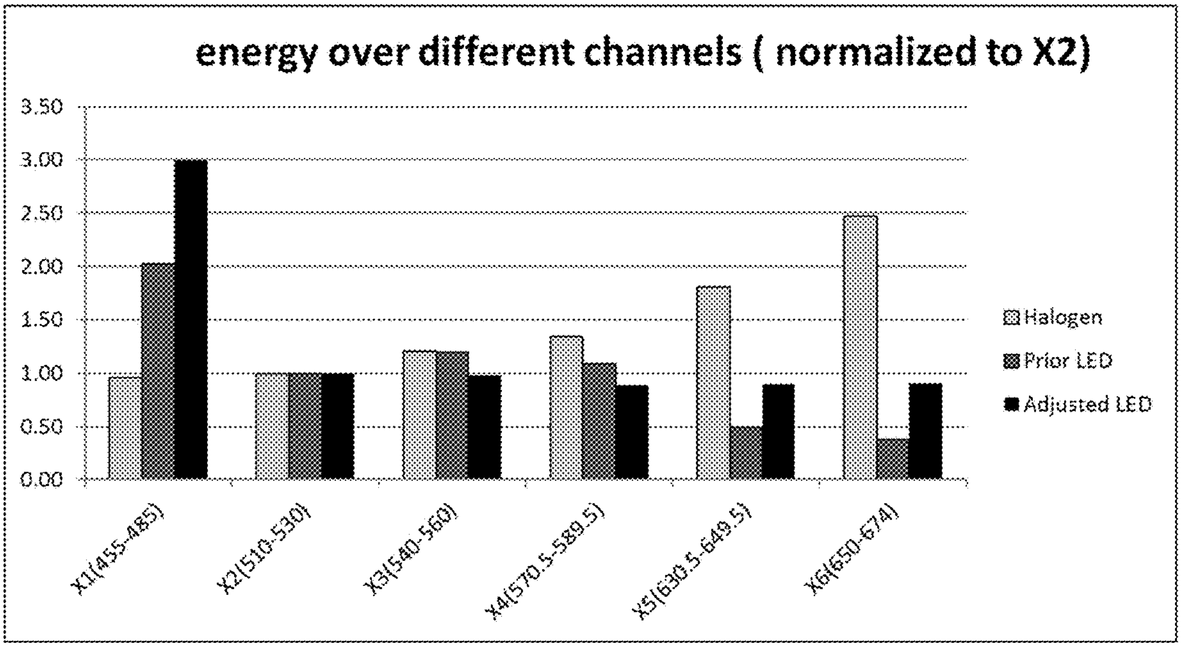
FIG. 4 is plot of spectral integration over various wavelength ranges for the light source spectrums shown in FIG. 3

Referring to FIGS. 3-4, the spectral distribution of radiation source 425 may be selected in a non-obvious manner to enable at least five excitation beams 405 of different colors or excitation channels to be used with one common beamsplitter 420, while simultaneously maintaining acceptable or predetermined data throughput for all excitation channels, for example, during each cycle of the qPCR assay. As used herein, the term "excitation channel" means each of several, distinct electromagnetic wavelength bands providing by an excitation source (e.g., excitation source 402) that are configured to illuminate one or more biological samples (e.g., biological samples 310). As used herein, the term "emission channel" means each of several, distinct emission wavelength bands over which electromagnetic radiation is allowed to pass onto an optical sensor or detector (e.g., optical sensor 408).

FIG. 3 shows the relative energy over the wavelength spectrum for three different radiation sources. The dashed line plot is the spectrum of a Halogen lamp (herein referred to as "Source 1") characterized by relatively low energy levels in the blue wavelength range of the visible spectrum and increasing energy until a peak at about 670 nanometers. The dash-dot spectrum plot is that of a commercially available LED light source (herein referred to as "Source 2"), which has peak energy at around 450 nanometers and a lower peak from about 530 nanometers to about 580 nanometers, then steadily decreasing energy into the red wavelength range of the visible spectrum. The solid line plot is the spectrum of another LED light source (herein referred to as "Source 3") according to an embodiment of the present invention (e.g., an exemplary spectrum for excitation source 402). FIG. 4 shows integrated energy over various excitation channels for each of the three sources shown in FIG. 3, where the spectrums for these channels are those of typical excitation filter used in the field of qPCR. The wavelength ranges and excitation filter designations are shown below in Table 1, where X1 is excitation channel 1, X2 is excitation channel 2, and so forth.

TABLE 1

Spectral bandwidth of excitation filters used in FIG. 4.

| Excitation Filter Channel | Wavelength Range (nanometers) |
|---|---|
| X1 | 455-485 |
| X2 | 510-530 |
| X3 | 540-560 |
| X4 | 570.5-589.5 |
| X5 | 630.5-649.5 |
| X6 | 650-674 |

In the field of qPCR, one important performance parameter is the total time to obtain emission data for samples containing multiple target dyes. For example, in some cases it is desirable to obtain emission data from multiple dyes or probes over one or more emission channels, designated M1-M6, for each excitation channel used to illuminate the sample(s) (e.g., M1-M6 with X1, M2-M6 with X2, M3-M6 with X3, M4-M6 with X4, M5-M6 with X5, and/or M6 with X6). The inventors have found that when Source 2 is used in a system having a single, broadband beamsplitter for five or six excitation/emission filter channels (e.g., excitation channels X1-X6 with combinations emission channels M1-M6), the amount of time to obtain data for excitation channel 5 and/or excitation channel 6 could be unacceptably long for certain applications. To remedy this situation, it is possible to use one or more narrow band, dichroic beamsplitters for excitation channels 1 and/or 2 to increase the amount of excitation light receive by the sample(s), and the amount of emission light received by the sensor (so that the overall optical efficiency is increased by using dichroic beam splitter, in this case). However, this precludes the use of a single beamsplitter arrangement, as shown in FIG. 1 and, therefore, the corresponding advantages of a single beamsplitter configuration (e.g., reduced size, cost, complexity) are lost. A better solution has been discovered in which a light source, such as Source 3, is used in combination with a single beamsplitter (e.g., a broadband beamsplitter such as a 50/50 beamsplitter), such as beamsplitter 420. It has been found that the relative energy in excitation channels X1, X5, and/or X6 may be used to identify an excitation source 402 suitable for use with a single beamsplitter embodiment to provide acceptable total integration time for collecting emission data over five or six excitation channels. Using LED Source 2 and LED Source 3 as examples, the following data shown in Table 2 below may be derived for the data shown in FIGS. 3 and 4.

TABLE 2

Normalized LED intensity of each filter channel with normalization over channel 2.

| Ratio | Source 2 | Source 3 |
|---|---|---|
| X1/X2 | 2.02 | 3.00 |
| X2/X2 | 1.00 | 1.00 |
| X3/X2 | 1.20 | 0.98 |
| X4/X2 | 1.09 | 0.89 |
| X5/X2 | 0.49 | 0.90 |
| X6/X2 | 0.38 | 0.90 |

Based on such data, the inventors have found that, in certain embodiments, improved performance (e.g., in terms of shorter Channel 1 integration time) may be obtain when X1/X2 is greater than 2.02 (e.g., greater than or equal to 3). Additionally or alternatively, in other embodiments, improved performance (e.g., in terms of shorter Channel 1 integration time) may be obtain when X5/X2 is greater than 0.49 (for example, greater than or equal to 0.9) and/or when X6/X2 is greater than 0.38 (for example, greater than or equal to 0.9). For the criteria set forth here, "X1" means an excitation channel that has a spectral output characterized by a maximum power, energy, or intensity within the wavelength band including 455-485 nanometers; "X2" means an excitation channel that has a spectral output characterized by a maximum power, energy, or intensity within the wavelength band including 510-530 nanometers; "X5" means an excitation channel that has a spectral output characterized by a maximum power, energy, or intensity within the wavelength band including 630.5-649.5 nanometers; "X6" means an excitation channel that has a spectral output characterized by a maximum power, energy, or intensity within the wavelength band including 650-674 nanometers Referring again to FIG. 1, excitation beams 405 are directed along excitation optical path 412 during operation toward sample processing base 300, for example, toward reaction regions 308 when sample holder 305 is present. When present, source lens 428 is configure to condition excitation beams 405, for example, to capture and direct a large portion of the emitted radiation from excitation source 402. In certain embodiments, one or more mirrors 432 (e.g., fold mirrors) may be incorporated along excitation optical path 412, for example, to make optical system 400 more compact and/or to provide predetermined package dimensions. FIG. 1 illustrated one mirror 432; however, addition mirrors may be used, for example to meet packaging design constraints. As discussed in greater detail below herein, additional lenses may be disposed near sample holder 305, for example, in order to further condition the excitation beams 405 and/or corresponding emissions from biological samples contained in one or more reaction regions.

Figure 8:
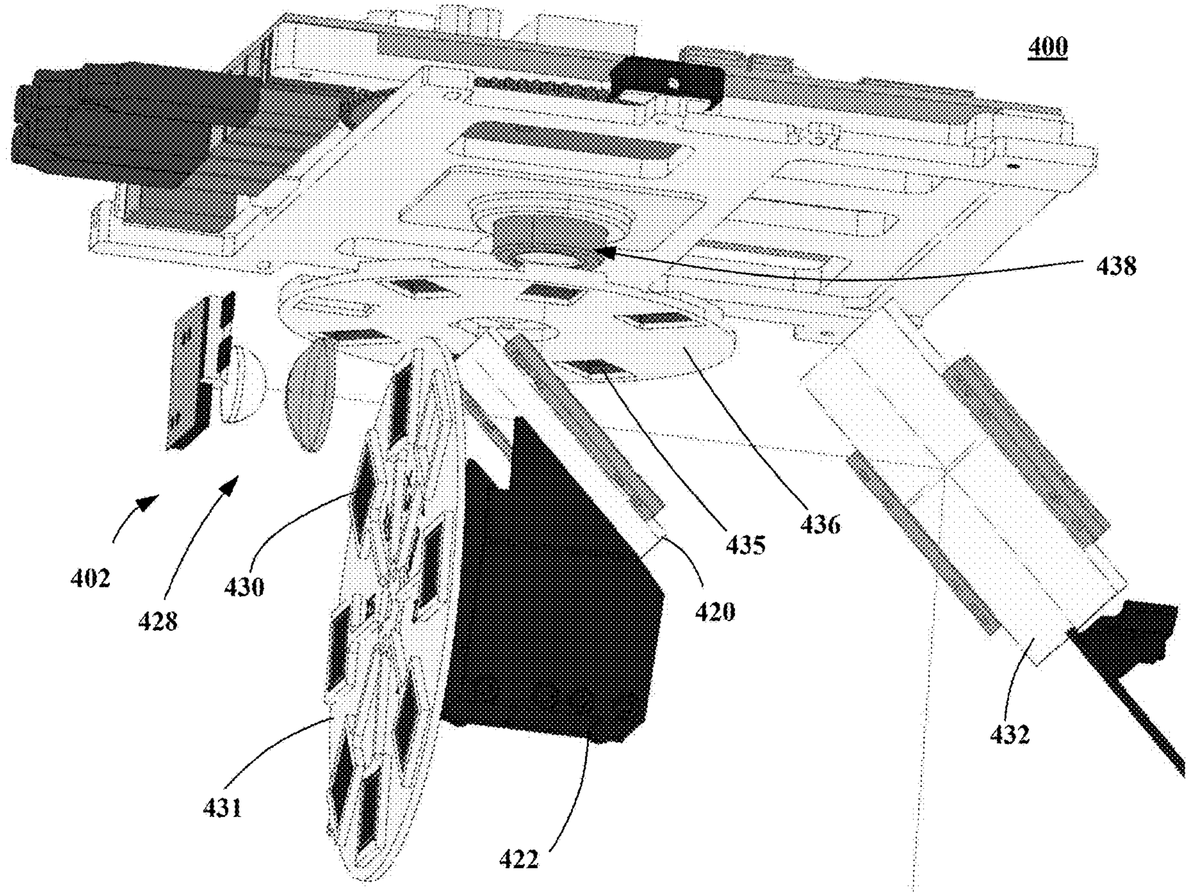
FIG. 8 is a magnified, solid model representation of the optical system shown in FIG. 7.

Emission optical system 415 is configured to direct emissions from the one or more biological samples to optical sensor 408. At least some of the emissions may comprise a fluorescent emission from at least some of the biological samples in response to at least one of the excitation beams 405. Additionally or alternatively, at least some of the emissions comprise radiation from at least one of the excitation beams 405 that is reflected, refracted, diffracted, scattered, or polarized by at least some of the biological samples. In certain embodiments, emission optical system 415 comprise one or more emission filters 435 configured, for example, to block excitation radiation reflected or scattered into emission optical path 417. In certain embodiments, there is a corresponding emission filter 435 for each excitation filter 430. Referring to FIG. 8, in certain embodiments, the excitation filter 430 are arranged in an excitation filter wheel 431 and/or the emission filters 435 are arranged in an emission filter wheel 436.

In certain embodiments, emission optical system 415 comprises a sensor lens 438 configured to direct emissions from at least some of the biological samples onto optical sensor 408. Optical sensor 408 may comprise a single sensor element, for example, a photodiode detector or a photomultiplier tube, or the like. Additionally or alternatively, optical sensor 408 may comprise an array sensor including an array of sensors or pixels. Array sensor 408 may comprise one or more of a complementary metal-oxide-semiconductor sensor (CMOS), a charge-coupled device (CCD) sensor, a plurality of photodiodes detectors, a plurality of photomultiplier tubes, or the like. Sensor lens 438 may be configured to from an image from the emissions from one or more of the plurality of biological samples 310. In certain embodiments, optical sensor 408 comprises two or more array sensors 408, for example, where two or more images are formed from the emissions from one or more of the plurality of biological samples 310. In such embodiments, emissions from one or more of the plurality of biological samples 310 may be split to provide two signals of the one or more of the plurality of biological samples 310. In certain embodiments, the optical sensor comprises at least two array sensors.

Beamsplitter 420 is disposed along both excitation and emission optical paths 412, 417 and is configured to receive both first and second excitation beams 405*a*, 405*b* during operation. In the illustrated embodiment shown in FIG. 1, beamsplitter 420 is configured to transmit the excitation beams 405 and to reflect emissions from the biological samples 310. Alternatively, beamsplitter 420 may be configured to reflect the excitation beams and to transmit emissions from the biological samples 310. In certain embodiments, beamsplitter 420 comprises a broadband beamsplitter having the same, or approximately the same, reflectance for all or most of the excitation beams 405 provided by excitation source 402 and directed to the reaction regions 308 (e.g., excitation beams 405*a*, 405*b* in the illustrated embodiment). For example, beamsplitter 420 may be a broadband beamsplitter characterized by a reflectance that is constant, or about constant, over a wavelength band of at least 100 nanometers, over a wavelength band of at least 200 nanometers, or over the visible wavelength band of the electromagnetic spectrum, over the visible and near IR wavelength bands of the electromagnetic spectrum, or over a wavelength band from 450 nanometers to 680 nanometers. In certain embodiments, beamsplitter 420 is a neutral density filter, for example, a filter having a reflectance of, or about, 20%, 50%, or 80% over visible wavelength band of the electromagnetic spectrum. In certain embodiments, beamsplitter 420 is a dichroic beamsplitter that is transmissive or reflective over one or more selected wavelength ranges, for example, a multi-wavelength band beamsplitter that is transmissive and/or reflective over more than one band of wavelengths centers at or near a peak wavelength of excitation beams 405.

In certain embodiments, beamsplitter 420 is a single beamsplitter configure to receive some or all of the plurality of excitation beams 405 (e.g., excitation beams 405*a*, 405*b*), either alone or in combination with a single beam dump 422. Each excitation beam may be referred to as an excitation channel, which may be used alone or in combination to excite different fluorescent dyes or probe molecule in one or more of the biological samples 310. By contrast many prior art systems and instruments, for example, in the field of qPCR, provide a plurality of excitation beams by using a separate beamsplitter and/or beam dump for each excitation channel and/or each emission channel of the system or instrument. In such prior art systems and instruments, chromatically selective dichroic filters are typically used in at least some of the excitation channels to increase the amount of radiation received at the samples. Disadvantages of systems and instruments using different beamsplitters and/or beam dumps for each channel include an increase in size, cost, complexity, and response time (e.g., dues to increased mass that must be moved or rotated when changing between excitation and/or emission channels). The inventors have discovered that it is possible to replace these plural beamsplitters and/or beam dumps with the single beamsplitter 420 and/or single beam dump 422, while still providing an acceptable or predetermined system or instrument performance, for example, by proper selection of spectral distribution of excitation source 402 and/or by configuring the systems or instruments to reduce the amount of stray or unwanted radiation received by optical sensor 408 (as discuss further herein). Thus, embodiments of the present invention may be used to provide systems and instruments that have reduced size, cost, complexity, and response time as compared to prior art systems and instruments.

Figure 5:
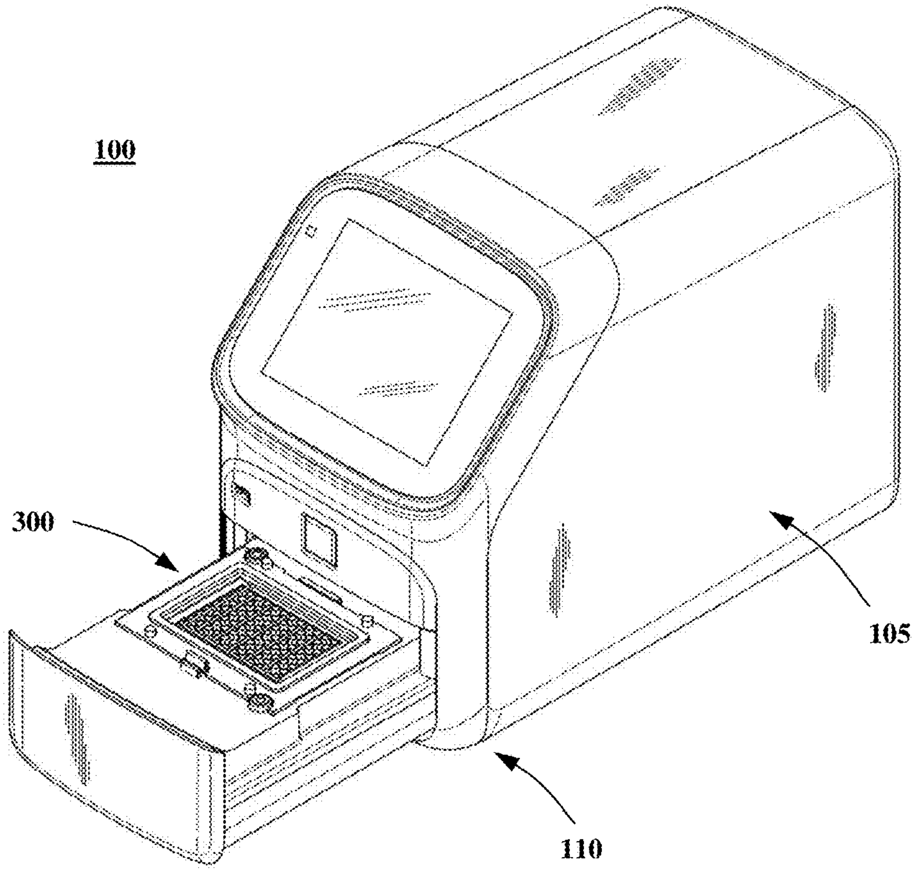
FIGS. 5 and 6 are perspective views of an instrument housing according to an embodiment of the present invention.
Figure 6:
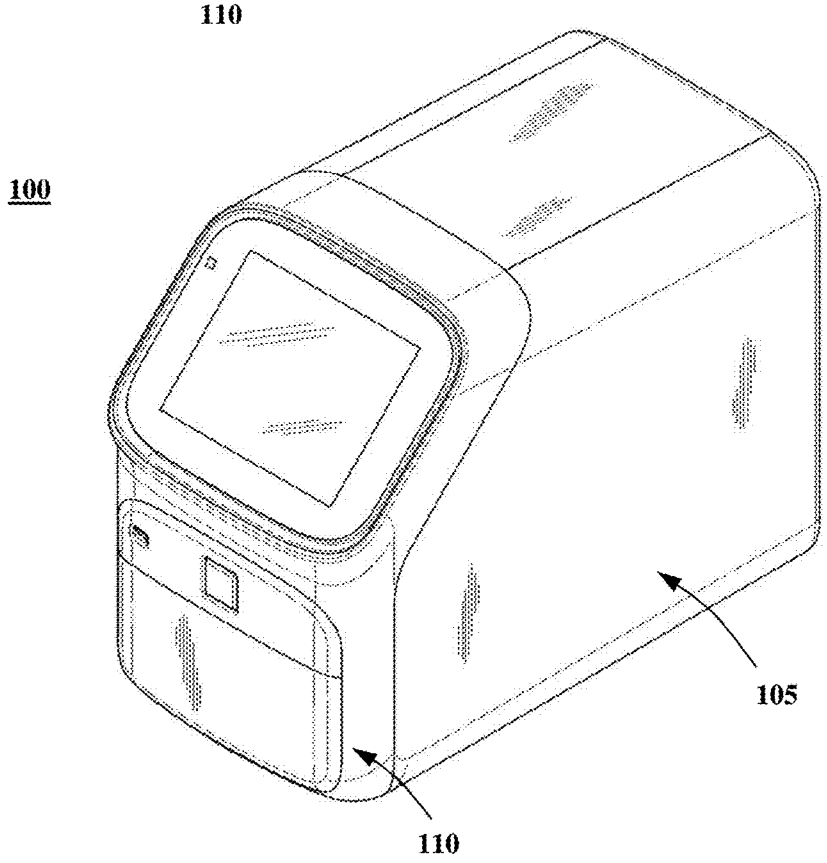

Referring to FIGS. 5 and 6, in certain embodiments, system 100 comprises an instrument housing 105 and sample holder drawer 110 comprising base 300 and configured during use to receive, hold, or contain sample holder 305 and to position sample holder 305 to provide optical coupling thereof with optical system 400. With drawer 110 closed (FIG. 6), housing 105 may be configured to contain or enclose sample processing system 300 and optical system 400. In certain embodiments, housing 105 may contain or enclose all or portions of electronic processor 200.

Figure 7:
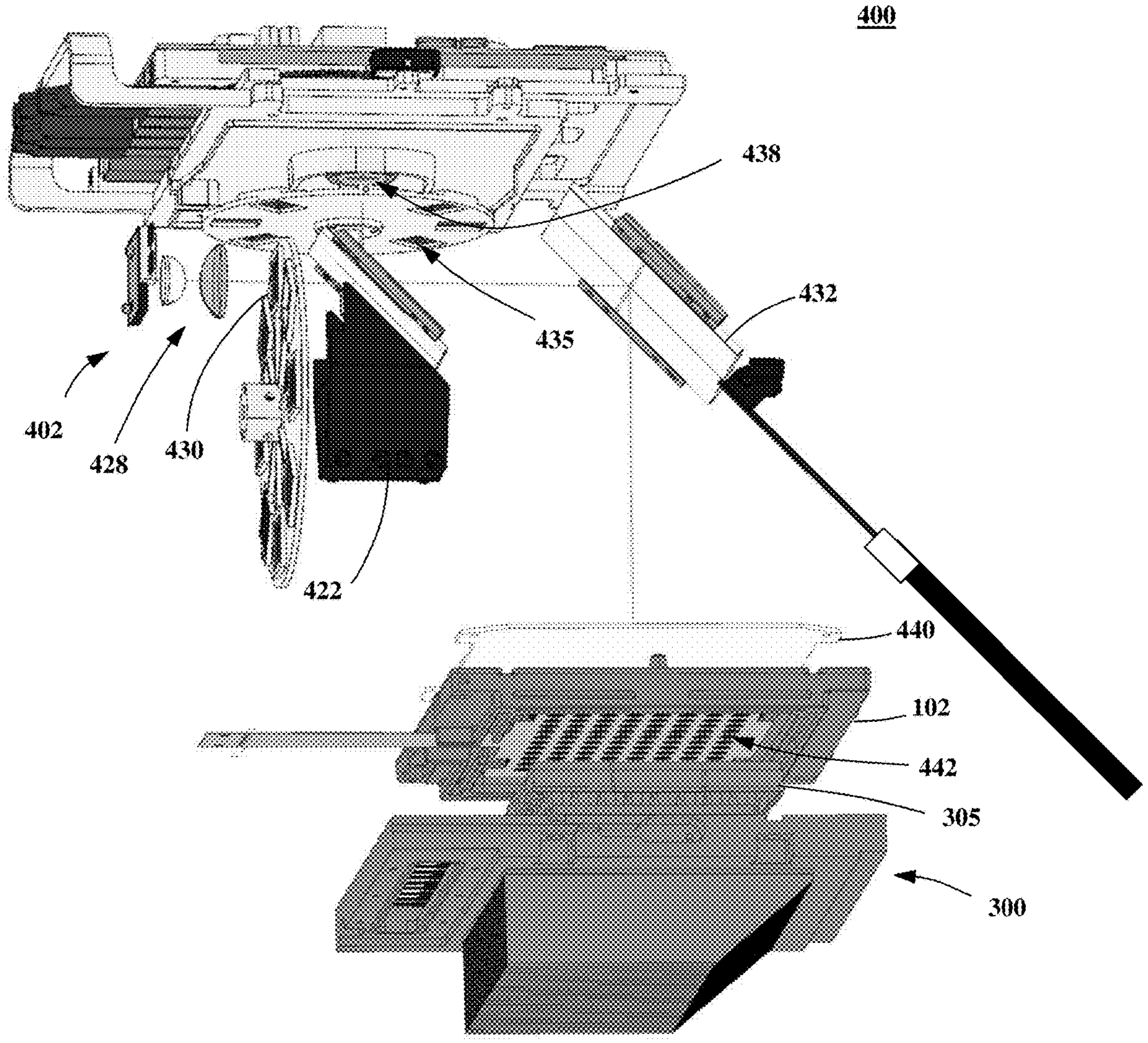
FIG. 7 is a solid model representation of an optical and sample processing system according to an embodiment of the present invention.
Figure 9:
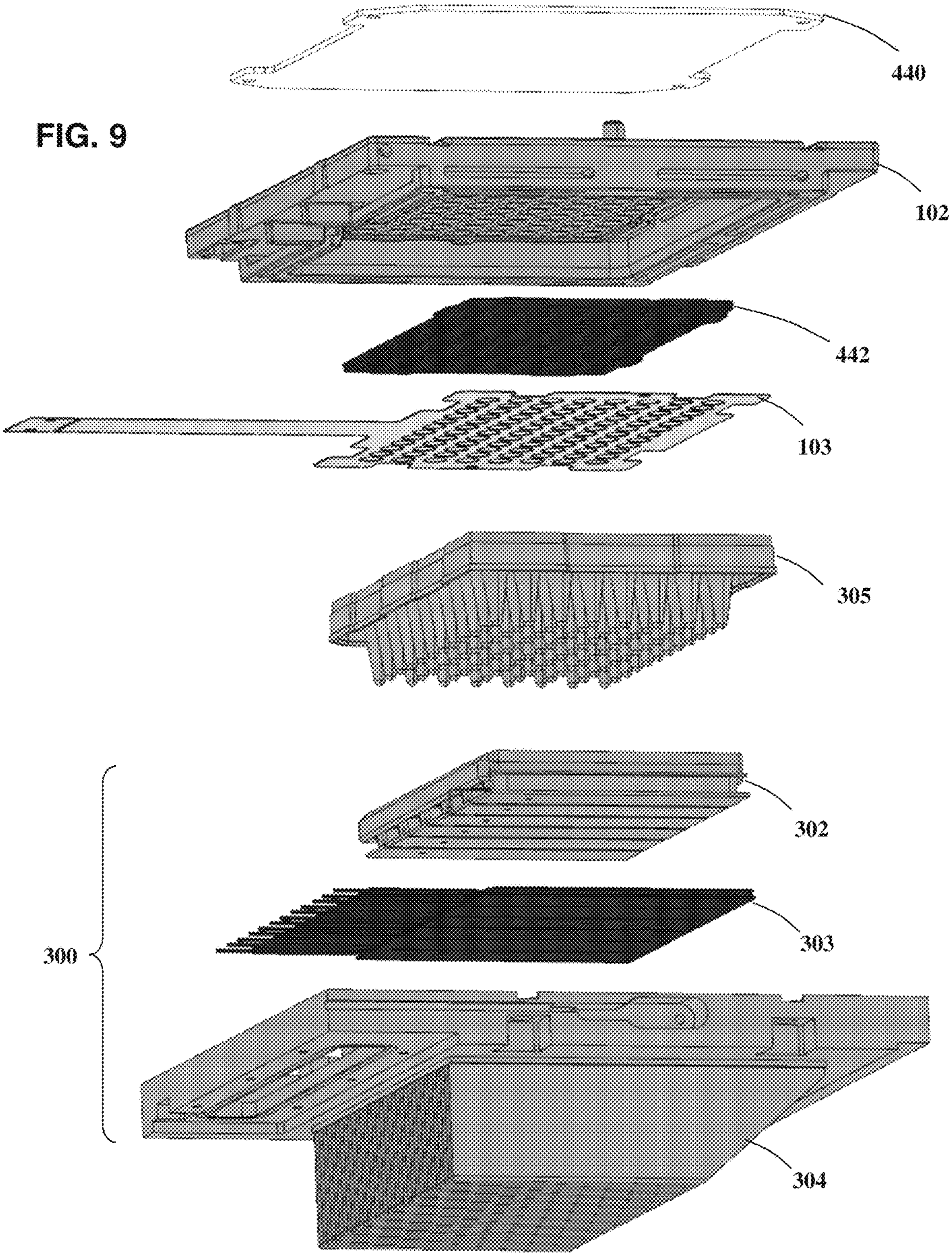
FIG. 9 is an exploded view of a portion of the sample processing system shown in FIG. 7.
Figure 11:
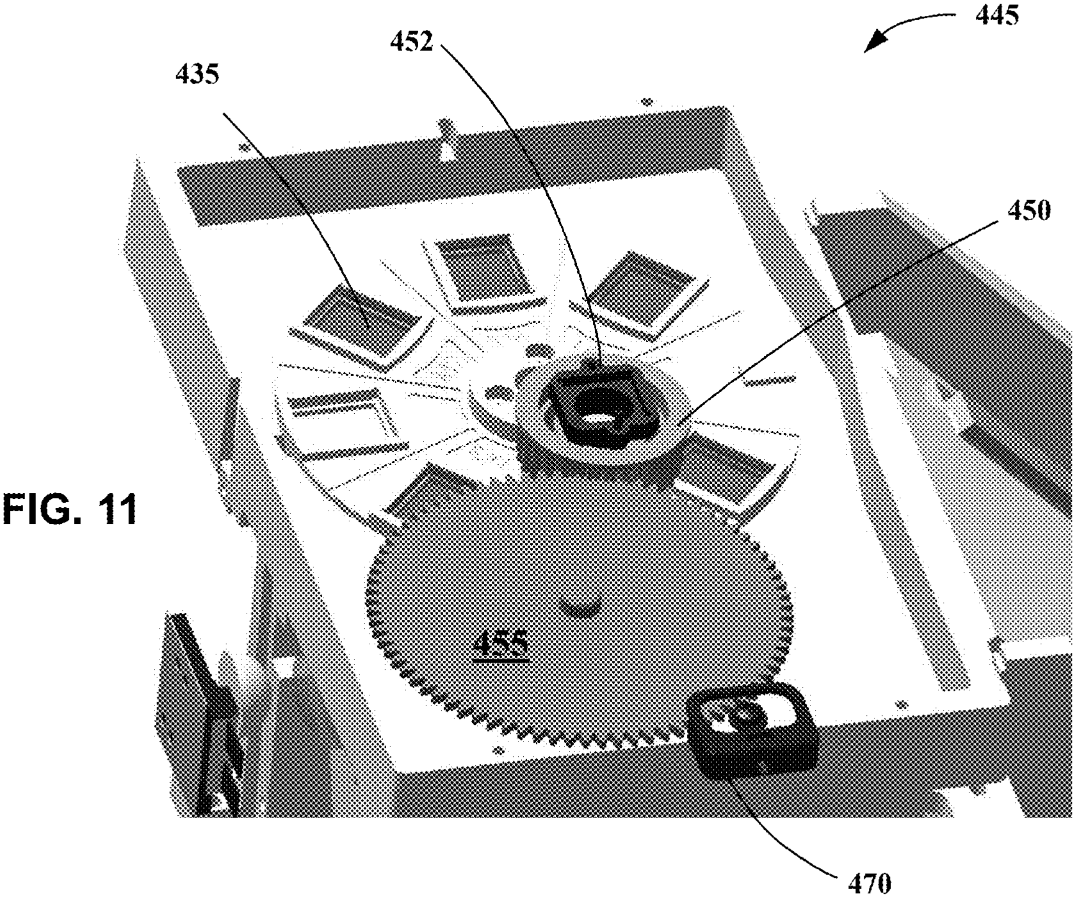
FIG. 11 is a top perspective view of an imaging unit according to an embodiment of the present invention.
Figure 12:
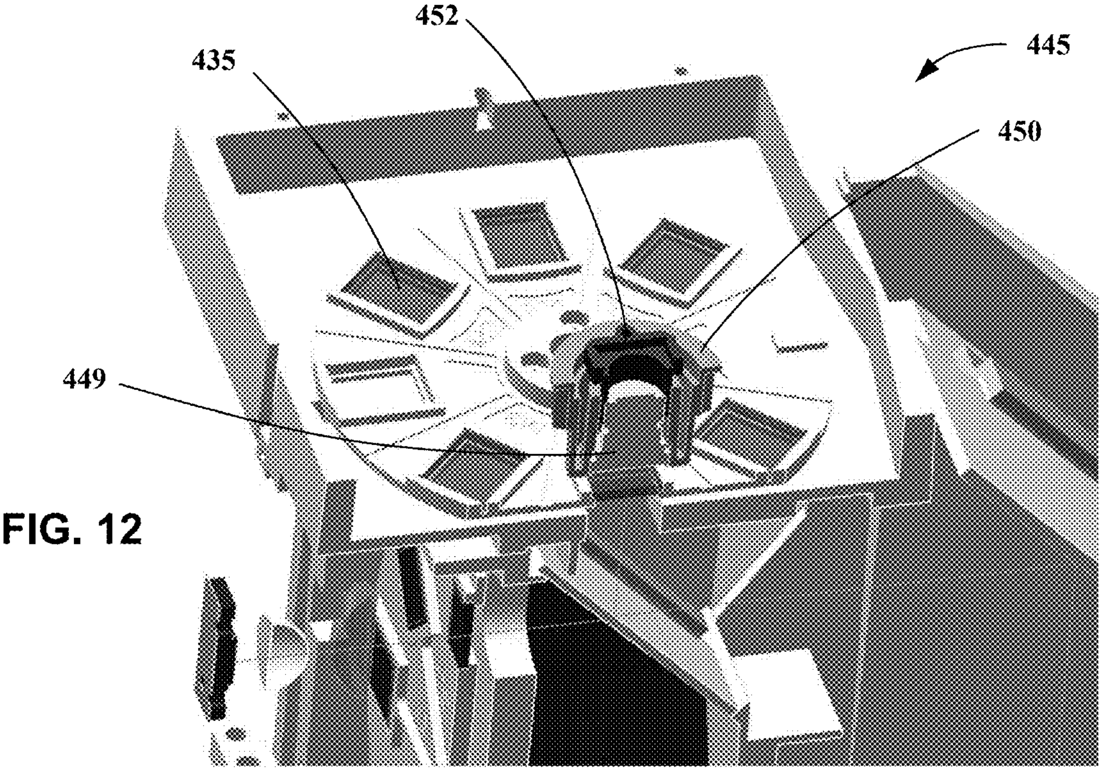
FIG. 12 is a sectional view of the imaging unit shown in FIG. 11
Figure 13:
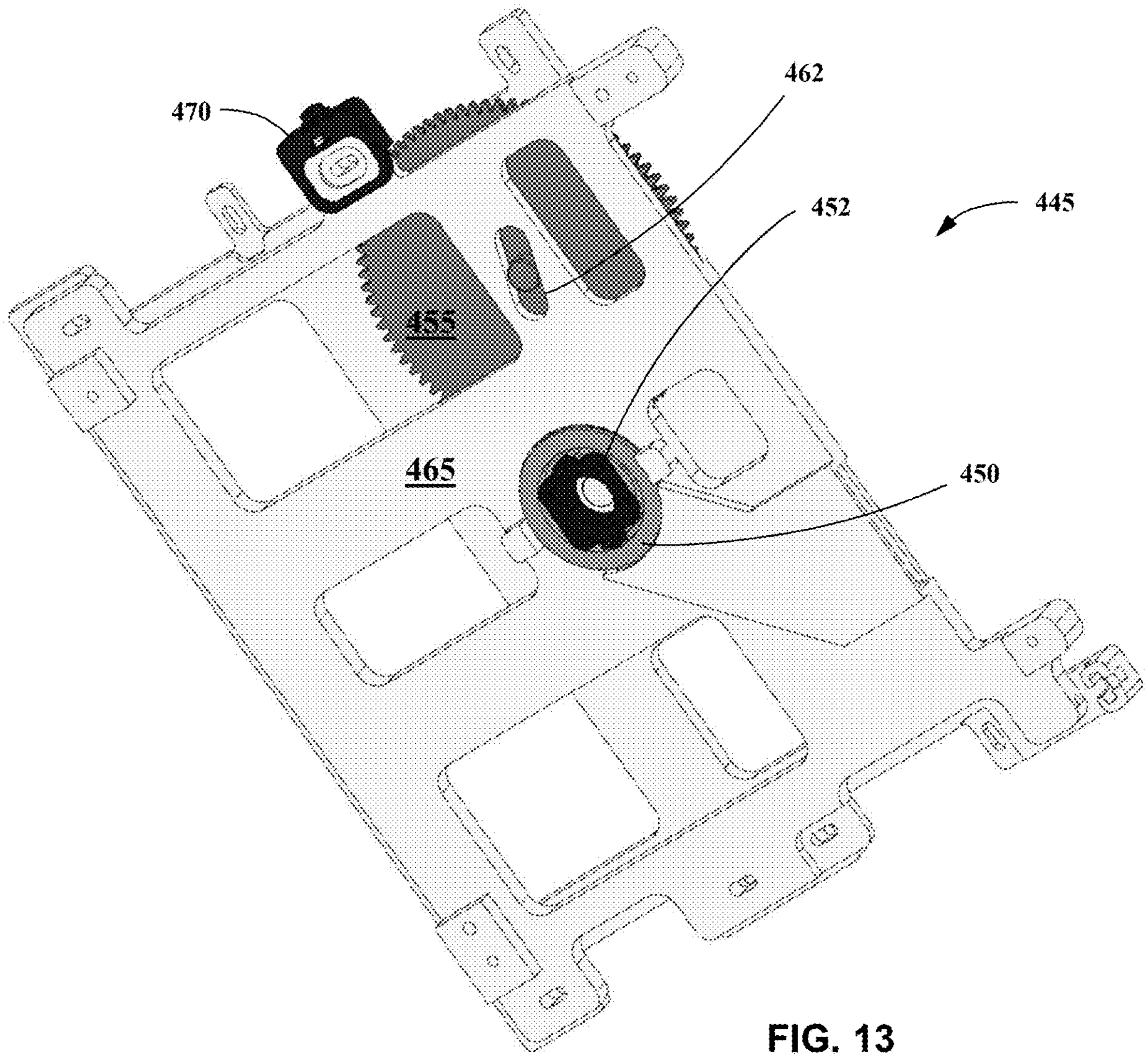
FIGS. 13 and 14 are bottom perspective views of the imaging unit shown in FIG. 11.

Referring to FIGS. 7-9, in certain embodiments, optical system 400 may further comprise a lens 440 and/or a lens array 442, which may comprise a plurality of lenses corresponding to each of the reaction regions 308 of sample holder 305. Lens 440 may comprise a field lens, which may be configured to provide a telecentric optical system for a least one of sample holder 305, reaction regions 308, lens array 442, or optical sensor 408. As shown in illustrated embodiment in FIGS. 7 and 9, lens 440 may comprise a Fresnel lens.

Referring again to FIGS. 7 and 9, in certain embodiments, base 300 comprises a sample block assembly 300 comprising a sample block 302, temperature controller 303, such as a Peltier device 303, and a heat sink 304. Sample block assembly 300 may be configured to provide a thermal controller or thermal cycling (e.g., provide a PCR assay or temperature profile), maintain a temperature of sample holder 305 or biological sample(s) 310, and/or otherwise maintain, control, adjust, or cycle heat flow or temperature of sample holder 305 or biological sample(s) 310.

Figure 14:
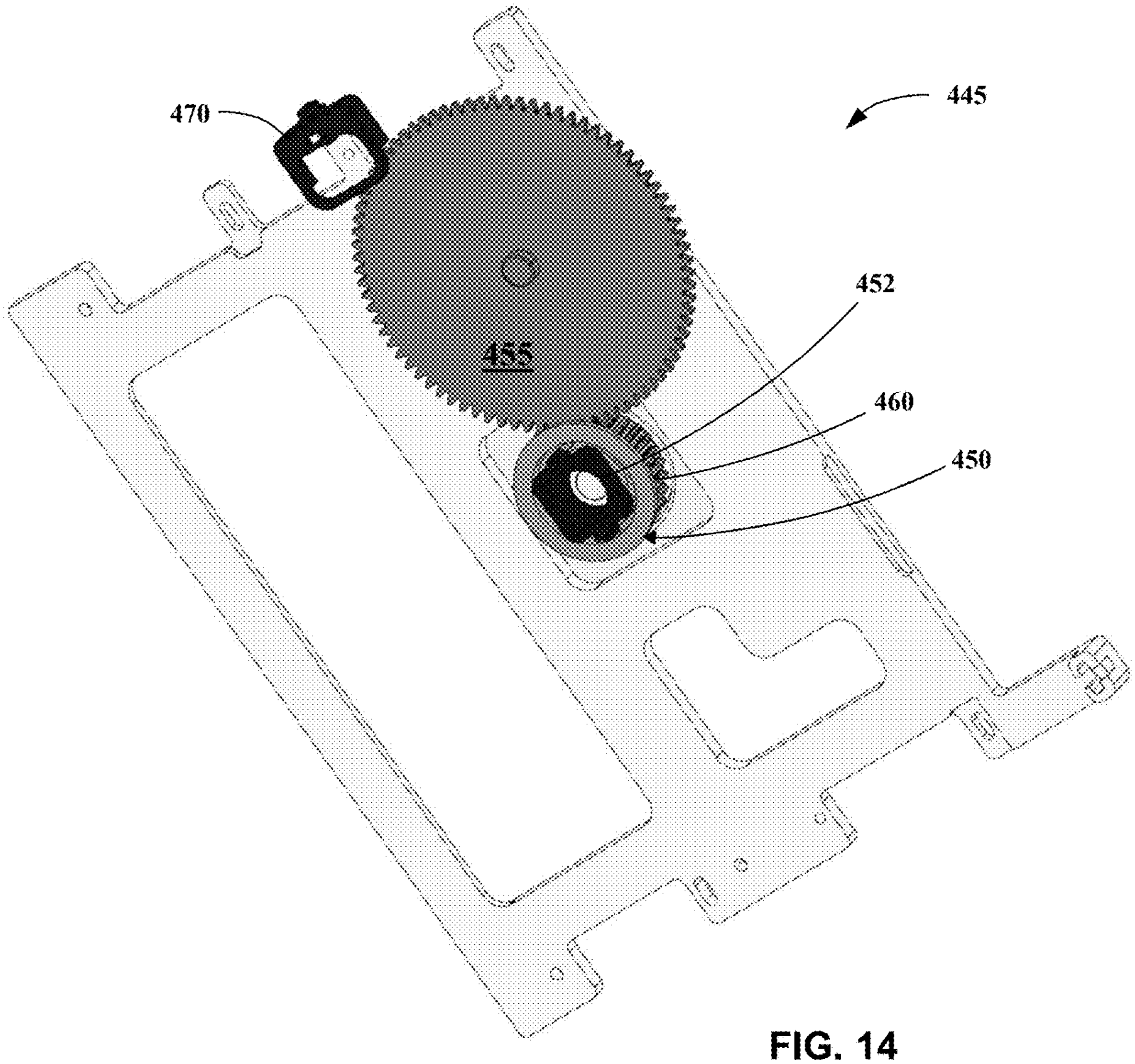

With additional reference to FIGS. 10-14, in certain embodiments, optical system 400 includes an imaging unit 445 comprising an optical sensor circuit board 448, sensor lens 438 (which may be a compound lens, as illustrated in FIG. 10), an inner lens mount 449, an outer lens mount 450, a threaded housing 452, and a focusing gear 455. Optical sensor circuit board 448, threaded housing 452, and sensor lens 438 together may form a cavity 458 that encloses or contains optical sensor 408 and may be configured to block any external light from impinging optical sensor 408 that does not enter through sensor lens 438. Outer lens mount 450 comprises an outer surface containing gear teeth 460 that may be moveably or slideably engaged with the teeth of focusing gear 455 via a resilient element (not shown), such as a spring. In certain embodiments, focusing gear 455 moves or slide along a slot 462 of a plate 465, as illustrated in FIG. 14. Inner lens mount 449 comprises a threaded portion 468 that engages or mates with a threaded portion of threaded housing 452.

Inner lens mount 449 may be fixedly mounted to outer lens mount 450, while threaded housing 452 is fixedly mounted relative to optical sensor circuit board 448. Inner lens mount 449 is moveably or rotatably mounted to threaded housing 452. Thus, focusing gear 455 and outer lens mount 450 may be engaged such that a rotation of focusing gear 455 also rotates outer lens mount 450. This, in turn, causes inner lens mount 449 and sensor lens 438 to move along an optical axis of sensor lens 438 via the threads in inner lens mount 449 and threaded housing 452. In this manner, the focus of sensor lens 438 may be adjusted without directly engaging sensor lens 438 or its associated mounts 449, 450, which are buried within a very compact optical system 400. Engagement with focusing gear 455 may be either by hand or automated, for example using a motor (not shown), such as a stepper motor or DC motor.

Referring to FIGS. 11 and 13-17, in certain embodiments, imaging unit 445 further comprises a locking device or mechanism 470. Locking device 470 comprises an edge or tooth 472 that may be slideably engaged between two teeth of focusing gear 455 (see FIGS. 15-17). As illustrated in FIGS. 15 and 16, locking device 470 may have a first position (FIG. 15) in which focusing gear 455 is free to rotate and adjust the focus of sensor lens 438 and a second position (FIG. 14) is which focusing gear 455 is locked in position and impeded or prevented from rotating. In this manner, the focus of sensor lens 438 may be locked while advantageously avoiding direct locking contact or engagement with threads 468 of inner lens mount 449, which could damage the threads and prevent subsequent refocusing of sensor lens 438 after being locked into position. Operation of locking device 470 may be either manually or in an automated manner. In certain embodiments, locking mechanism 470 further comprises a resilient element such as a spring (not shown), wherein rotation of focusing gear 455 may be accomplished by overcoming a threshold force produced by the resilient element.

Figure 18:
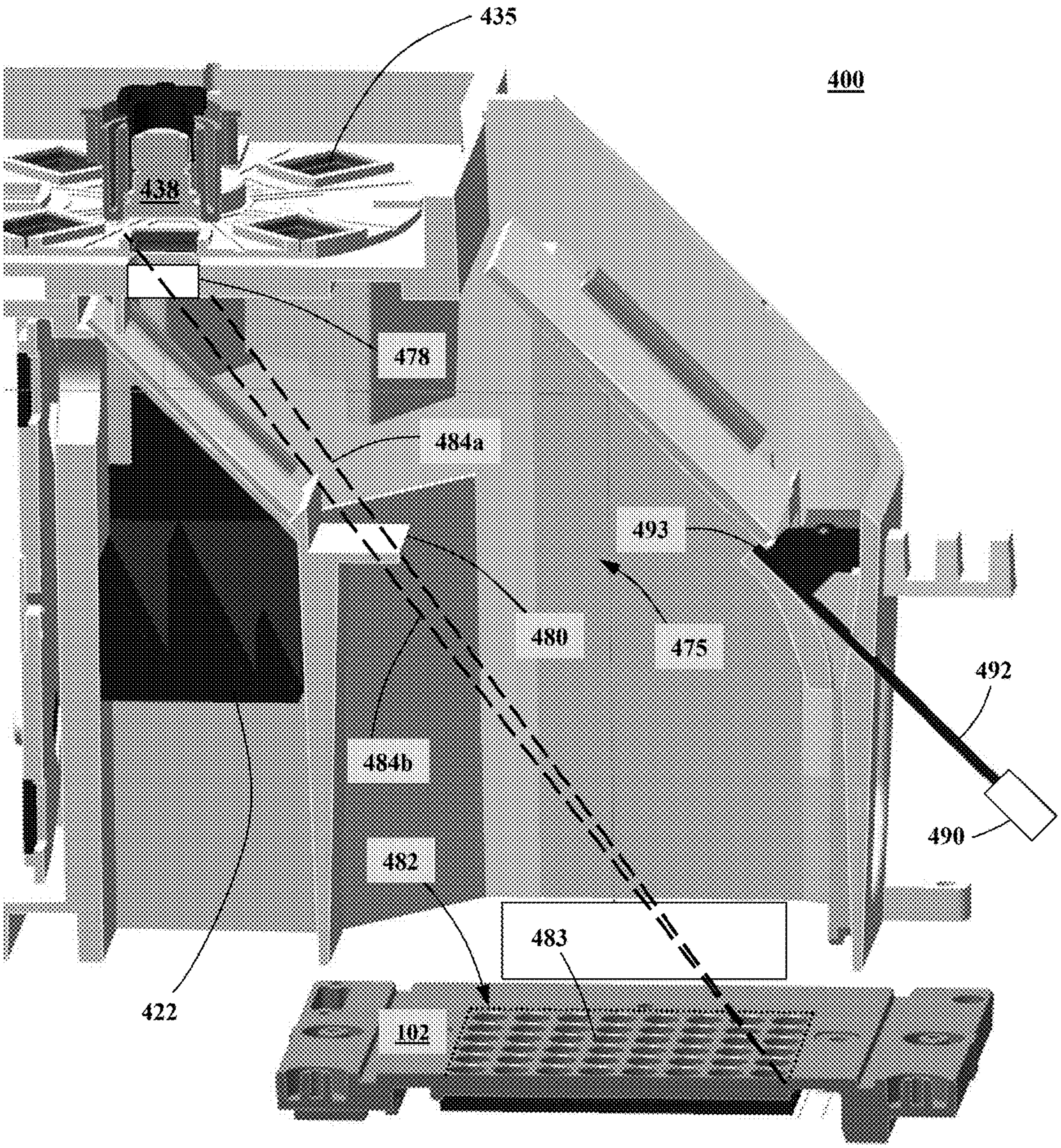
FIG. 18 is a section view of the system shown in FIGS. 6 and 8.

Referring to FIG. 18, optical system 400 may also include an optics housing 477. In certain embodiments, optical system 400 includes a radiation shield 475 comprising a sensor aperture 478 disposed along emission optical path 417 and at least one blocking structure 480 disposed to cooperate with sensor aperture 478 such that the only radiation from excitation beams 405, and reflected off an illuminated surface or area 482, to pass through sensor aperture 478 is radiation that has also reflected off at least one other surface of, or within, the optics housing 477. In other words, radiation shield 475 is configured such that radiation from excitation beams 405 reflected illuminated area 482 are blocked from directly passing through aperture 478 and, therefore, from passing into sensor lens 438 and onto optical detector 408. In certain embodiments, illuminated area 482 comprises the area defined by all the apertures 483 of heated cover 102 corresponding to the plurality of reaction regions 308.

In the illustrated embodiment of FIG. 18, blocking structure 480 comprises a shelf 480. Dashed lines or rays 484*a* and 484*b* may be used to illustrate the effectiveness of blocking structure 480 in preventing light directly reflected from illuminated area 482 from passing through sensor aperture 478 and onto senor lens 438 and/or optical sensor 408. Ray 484*a* originates from an edge of illuminated area 482 an just passes shelf 480, but does not pass through sensor aperture 478. Ray 484*b* is another ray originating from the same edge of illuminated area 482 that is blocked by shelf 480. As can be seen, this ray would have entered through sensor aperture 478 were it not for the presences of shelf 480.

With continued reference to FIG. 18, in certain embodiments, optical system 400 may further comprise an energy or power detection unit comprising a power or energy sensors 490 optically coupled to one end of a light pipe 492. An opposite end 493 of light pipe 492 is configured to be illuminated by excitation beams 405. Light pipe end 493 may be illuminated either directly by radiation contained in excitation beams 405 or indirectly, for example, by radiation scattered by a diffuse surface. In certain embodiments, sensor 490 is located outside of the excitation optical path 412 from excitation source 402. Additionally or alternatively, sensor 490 is located outside optics housing 477 and/or is located at a remote location outside instrument housing 105. In the illustrated embodiment shown in FIG. 18, light pipe end 493 is disposed near or adjacent mirror 432 and may be oriented so that the face of the light pipe is perpendicular, or nearly perpendicular, to the surface of mirror 432 that reflects excitation beams 405. The inventors have discovered that the low amount of energy or power intercepted by light pipe 492 when oriented in this way is sufficient for the purpose of monitoring the energy or power of excitation beams 405. Advantageously, by locating sensor 490 outside the optical path of excitation beams a more compact optical system 400 may be provided.

In certain embodiments, light pipe 492 comprises a single fiber or a fiber bundle. Additionally or alternatively, light 492 may comprise a rod made of a transparent or transmissive material such as glass, Plexiglas, polymer based material such as acrylic, or the like.

Figure 19:
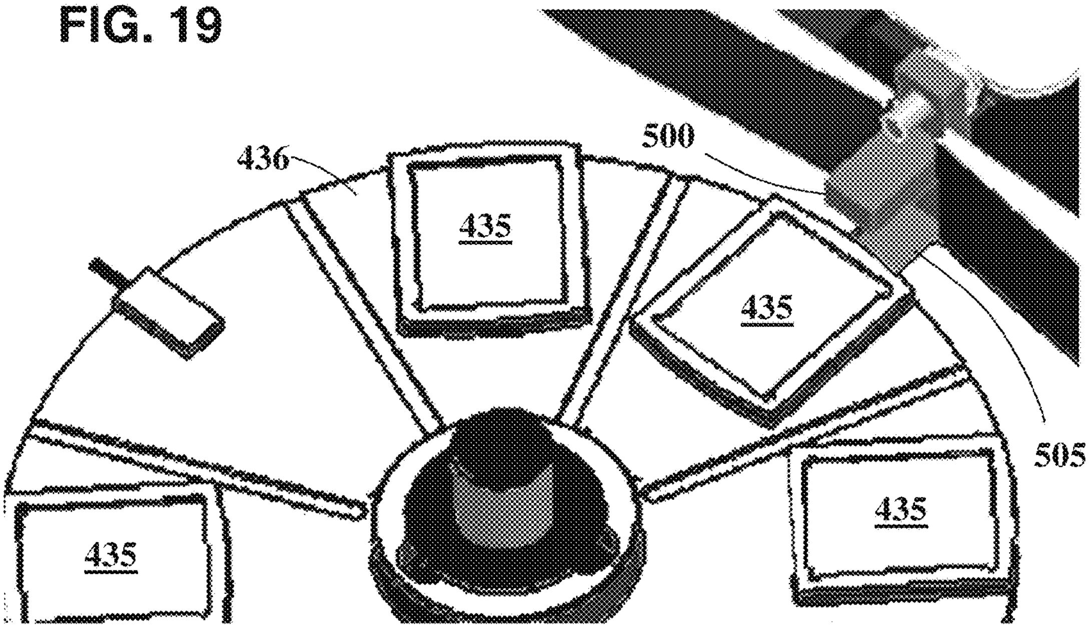
FIGS. 19 and 20 are schematic representations of a system according to an embodiment of the present invention.
Figure 20:
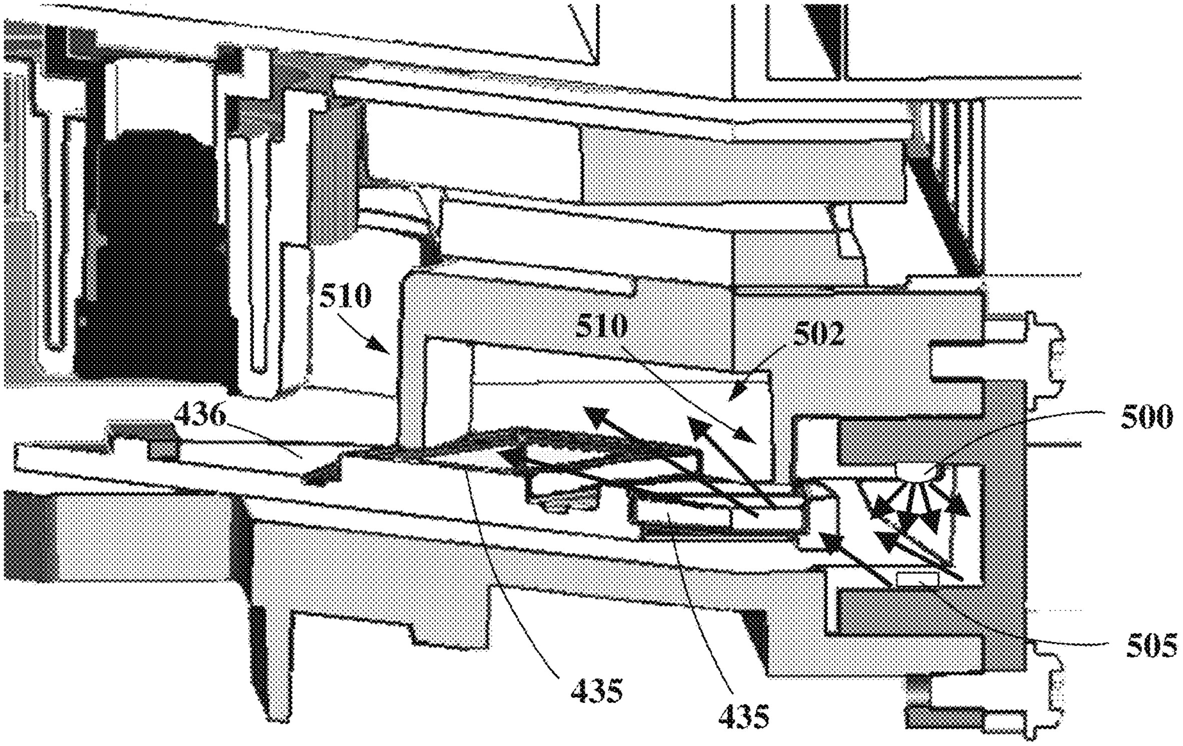

Referring to FIGS. 19 and 20, in certain embodiments instrument 100 comprises a position source 500 configured to emit radiation 502 and a corresponding position sensor 505 configured to receive radiation 502 from position source 500. Position source 500 and position sensor 505 may be configured to produce a position signal indicative of a position of an optical element 435 disposed along optical paths. In certain embodiments, instrument 100 may further comprise a radiation shield 510 configured to block at least some radiation 502 from position source 505.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

Exemplary systems for methods related to the various embodiments described in this document include those described in following applications:

U.S. design patent application Ser. No. 29/516,847, filed on Feb. 6, 2015; and

U.S. design patent application Ser. No. 29/516,883; filed on Feb. 6, 2015; and

U.S. provisional patent application No. 62/112,910, filed on Feb. 6, 2015; and

U.S. provisional patent application No. 62/113,006, filed on Feb. 6, 2015; and

U.S. provisional patent application No. 62/113,183, filed on Feb. 6, 2015; and

U.S. provisional patent application No. 62/113,077, filed on Feb. 6, 2015; and

U.S. provisional patent application No. 62/113,058, filed on Feb. 6, 2015; and

U.S. provisional patent application No. 62/112,964, filed on Feb. 6, 2015; and

U.S. provisional patent application No. 62/113,118, filed on Feb. 6, 2015; and

U.S. provisional patent application No. 62/113,212, filed on Feb. 6, 2015; and

U.S. patent application Ser. No. 15/017,136, filed on Feb. 5, 2016; and

U.S. patent application Ser. No. 15/017,249, filed on Feb. 5, 2016; and

U.S. patent application Ser. No. 15/016,485, filed on Feb. 5, 2016; and

U.S. patent application Ser. No. 15/016,564, filed on Feb. 5, 2016; and

U.S. patent application Ser. No. 15/016,713, filed on Feb. 5, 2016; and

U.S. patent application Ser. No. 15/017,034, filed on Feb. 5, 2016; and

U.S. patent application Ser. No. 15/017,393, filed on Feb. 5, 2016, all of which are also herein incorporated by reference in their entirety.

What is claimed is:

1. An instrument for biological analysis, comprising:

an excitation source;

an optical sensor configured to receive emissions from one or more biological samples in response to the excitation source;

an excitation optical system disposed along an excitation optical path;

an emission optical system disposed along an emission optical path;

a sensor lens configured to direct emissions from at least some of the biological sample onto the optical sensor;

a heated cover disposed in the excitation path configured to prevent condensation above the biological samples contained in a sample holder, the heated cover having an illuminated surface disposed along the excitation optical path, the illuminated surface configured to produce reflected radiation comprising radiation from the excitation source that is reflected by the illuminated surface; and a radiation shield, wherein:

the radiation shield comprises a sensor aperture disposed along the emission optical path and a blocking structure configured to cooperate with the sensor aperture such that, of the radiation which is reflected by the illuminated surface, only that is subsequently reflected by another surface of the instrument is received by the optical sensor.

2. The instrument according to claim 1, further comprising a beamsplitter disposed along both the excitation optical path and along the emission optical path.

3. The instrument according to claim 2, further comprising:

a base configured to receive a sample holder comprising a plurality of spatially separated reaction regions for processing the one or more biological samples, wherein:

the excitation optical path is between the excitation source and the sample holder;

the emission optical path is between the sample holder and the optical sensor;

the emission optical system is configured to direct the emissions from the biological samples to the optical sensor;

the illuminated surface is disposed along the excitation optical path between the beamsplitter and the base; and the sensor aperture is disposed between the beamsplitter and the sensor lens.

4. The instrument according to claim 3, wherein the base comprises a thermal controller.

5. The instrument according to claim 4, wherein the thermal controller is configured to control a temperature of at least one of the base, the sample holder, or the separated biological samples, or the thermal controller comprises a thermal cycler configured to perform a PCR assay.

6. The instrument according to claim 3, wherein the heated cover is disposed adjacent the base, the heated cover including a plurality of apertures configured to correspond to the plurality of reaction regions.

7. The instrument according to claim 3, wherein the excitation optical system comprises a sample lens configured to direct the excitation beams toward the base;

the sample lens comprises a field lens configured to extend over the plurality of spatially separated regions; and the sample lens is configured to provide a telecentric optical system for a least one of the sample holder, the spatially separated reaction regions, or the optical sensor.

8. The instrument according to claim 2, wherein the beamsplitter is characterized by a reflectance that is constant over a wavelength band from 450 nanometers to 680 nanometers.

9. The instrument according to claim 1, wherein the blocking structure is configured to cooperate with the sensor aperture such that none of the reflected radiation impinges on the sensor lens that does not also reflect off another surface of the instrument.

10. The instrument according to claim 1, wherein the excitation source is configured to provide a plurality of excitation beams to illuminate the biological samples, and at least some of the emissions optionally comprising a fluorescent emission from at least some of the biological samples in response to at least one of plurality of the excitation beams.

11. The instrument according to claim 10, wherein the excitation source is configured to produce a first excitation beam characterized by a first wavelength and a second excitation beam characterized by a second wavelength that is different from the first wavelength.

12. The instrument according to claim 11, wherein the first excitation beam and the second excitation beam are temporally separated and/or spatially separated.

13. The instrument according to claim 10, wherein the plurality of excitation beams comprises a first excitation beam that comprises a first wavelength range over which an intensity, power, or energy of the first excitation beam is above a first predetermined value, and a second excitation beam that comprises a second wavelength range over which an intensity, power, or energy of the second excitation beam is above a second predetermined value, the first wavelength being at least one of:

(1) a central wavelength of the first wavelength range or (2) a wavelength of maximum electromagnetic intensity, power, or energy over the first wavelength range, and the second wavelength being at least one of (1) a central wavelength of the second wavelength range; or (2) a wavelength of maximum electromagnetic intensity, power, or energy over the second wavelength range.

14. The instrument according to claim 1, wherein the excitation source comprises a plurality of individual excitation sources, and the plurality of individual excitation sources optionally forming a two-dimensional array of individual excitation sources.

15. The instrument according to claim 1, wherein the optical sensor comprises an array sensor, the array sensor optionally comprising at least one of a complementary metal-oxide-semiconductor sensor or a charge-coupled device sensor, and the optical sensor optionally comprising at least two array sensors.

* * * * *